United States Patent
Sahatjian et al.

(10) Patent No.: US 8,784,465 B2
(45) Date of Patent: Jul. 22, 2014

(54) IMPLANTABLE MEDICAL DEVICES

(75) Inventors: Ronald A. Sahatjian, Lexington, MA (US); Francisca Tan, Boston, MA (US); Patrick T. Mather, Chagrin Falls, OH (US); Changdeng Liu, Storrs, CT (US); Cheryl J. Campo, Cleveland Heights, OH (US)

(73) Assignees: Boston Scientific Scimed, Inc., Maple Grove, MN (US); University of Connecticut, Farmington ( * ) Notice: Subject to any disclaimer, the term of this patent is extended or adjusted under 35 U.S.C. 154(b) by 152 days.

(21) Appl. No.: 12/940,388

(22) Filed: Nov. 5, 2010

(65) Prior Publication Data

US 2011/0054591 A1 Mar. 3, 2011

Related U.S. Application Data

(60) Division of application No. 12/880,483, filed on Sep. 13, 2010, which is a division of application No. 10/958,435, filed on Oct. 5, 2004, now Pat. No. 7,794,494, which is a continuation-in-part of application No. 10/683,314, filed on Oct. 10, 2003, now abandoned.

(60) Provisional application No. 60/418,023, filed on Oct. 11, 2002, provisional application No. 60/488,323, filed on Jul. 18, 2003, provisional application No. 60/419,506, filed on Oct. 18, 2002, provisional application No. 60/466,401, filed on Apr. 29, 2003, provisional application No. 60/488,590, filed on Jul. 18, 2003.

(51) Int. Cl.
| | | |
|---|---|---|
| *A61F 2/06* | (2013.01) | |
| *A61F 2/88* | (2006.01) | |
| *A61F 2/915* | (2013.01) | |
| *A61L 29/14* | (2006.01) | |
| *C08L 65/00* | (2006.01) | |
| *C08G 18/42* | (2006.01) | |
| *C08G 61/08* | (2006.01) | |
| *A61F 2/91* | (2013.01) | |
| *C08G 18/38* | (2006.01) | |
| *A61L 31/14* | (2006.01) | |
| *C08G 18/48* | (2006.01) | |
| *A61F 2/848* | (2013.01) | |
| *A61F 2/95* | (2013.01) | |
| *A61M 25/10* | (2013.01) | |

(52) U.S. Cl.
CPC ......... *C08G 61/08* (2013.01); *A61F 2002/8483* (2013.01); *A61F 2250/0068* (2013.01); *A61F 2/88* (2013.01); *A61F 2/915* (2013.01); *C08G 2230/00* (2013.01); *A61F 2002/91541* (2013.01); *A61L 29/14* (2013.01); *A61F 2250/0039* (2013.01); *C08L 65/00* (2013.01); *A61F 2002/9528* (2013.01); *C08G 18/4277* (2013.01); *A61F 2/91* (2013.01); *C08G 18/3893* (2013.01); *A61L 31/14* (2013.01); *A61M 25/1027* (2013.01); *C08G 18/4833* (2013.01)
USPC ........... 623/1.1; 623/1.18; 623/1.19; 623/1.2; 623/1.46; 264/305; 264/510

(58) Field of Classification Search
USPC ................ 427/2.24–2.27; 424/422; 623/1.11, 623/1.12, 1.15, 1.46; 606/191–198; 526/171, 90, 135, 308; 525/98, 131, 525/216, 231, 240, 241, 387
See application file for complete search history.

(56) References Cited

U.S. PATENT DOCUMENTS

| | | | |
|---|---|---|---|
| 3,383,336 | A | 5/1968 | Kuyama et al. |
| 3,459,725 | A | 8/1969 | Natta et al. |
| 3,563,973 | A | 2/1971 | Arditti et al. |
| 4,080,357 | A | 3/1978 | Gergen et al. |
| 4,503,569 | A | 3/1985 | Dotter |
| 4,531,933 | A | 7/1985 | Norton et al. |
| 4,612,241 | A | 9/1986 | Howard, Jr. |
| 4,893,623 | A | 1/1990 | Rosenbluth |
| 4,950,258 | A | 8/1990 | Kawai et al. |
| 4,969,890 | A | 11/1990 | Sugita et al. |

| | | | |
|---|---|---|---|
| 4,990,155 A * | 2/1991 | Wilkoff | 606/191 |
| 5,007,926 A | 4/1991 | Derbyshire | |
| 5,037,427 A | 8/1991 | Harada et al. | |
| 5,062,829 A | 11/1991 | Pryor et al. | |
| 5,064,435 A | 11/1991 | Porter | |
| 5,089,005 A | 2/1992 | Harada | |
| 5,100,429 A | 3/1992 | Sinofsky et al. | |
| 5,145,935 A | 9/1992 | Hayashi | |
| 5,147,385 A | 9/1992 | Beck et al. | |
| 5,163,952 A | 11/1992 | Froix | |
| 5,189,110 A | 2/1993 | Ikematu et al. | |
| 5,258,020 A | 11/1993 | Froix | |
| 5,278,237 A | 1/1994 | Kita | |
| 5,282,854 A | 2/1994 | Yagi et al. | |
| 5,395,882 A | 3/1995 | Siol et al. | |
| 5,421,955 A | 6/1995 | Lau et al. | |
| 5,461,114 A | 10/1995 | Kita | |
| 5,466,242 A | 11/1995 | Mori | |
| 5,496,311 A | 3/1996 | Abele et al. | |
| 5,506,300 A | 4/1996 | Ward et al. | |
| 5,603,722 A | 2/1997 | Phan et al. | |
| 5,607,467 A | 3/1997 | Froix | |
| 5,645,559 A | 7/1997 | Hachtman et al. | |
| 5,665,822 A | 9/1997 | Bitler et al. | |
| 5,670,161 A * | 9/1997 | Healy et al. | 623/1.42 |
| 5,674,241 A | 10/1997 | Bley et al. | |
| 5,674,242 A * | 10/1997 | Phan et al. | 606/198 |
| 5,741,333 A | 4/1998 | Frid | |
| 5,755,769 A | 5/1998 | Richard et al. | |
| 5,762,625 A | 6/1998 | Igaki | |
| 5,766,188 A | 6/1998 | Igaki | |
| 5,769,883 A | 6/1998 | Buscemi et al. | |
| 5,776,162 A | 7/1998 | Kleshinski | |
| 5,800,516 A | 9/1998 | Fine et al. | |
| 5,817,100 A | 10/1998 | Igaki | |
| 5,830,179 A | 11/1998 | Mikus et al. | |
| 5,833,651 A * | 11/1998 | Donovan et al. | 604/509 |
| 5,843,096 A | 12/1998 | Igaki et al. | |
| 5,849,037 A | 12/1998 | Frid | |
| 5,876,432 A | 3/1999 | Lau et al. | |
| 5,880,240 A | 3/1999 | Tsuno | |
| 5,889,118 A | 3/1999 | Delgado et al. | |
| 5,900,246 A | 5/1999 | Lambert | |
| 5,908,918 A | 6/1999 | Chen et al. | |
| 5,910,357 A | 6/1999 | Hachisuka et al. | |
| 5,928,217 A | 7/1999 | Mikus et al. | |
| 5,935,506 A | 8/1999 | Schmitz et al. | |
| 5,954,744 A | 9/1999 | Phan et al. | |
| 5,955,559 A | 9/1999 | Handlin, Jr. et al. | |
| 5,961,547 A | 10/1999 | Razavi | |
| 5,964,744 A | 10/1999 | Balbierz et al. | |
| 5,968,070 A | 10/1999 | Bley et al. | |
| 5,997,563 A | 12/1999 | Kretzers | |
| 6,024,764 A | 2/2000 | Schroeppel | |
| 6,033,413 A | 3/2000 | Mikus et al. | |
| 6,045,568 A | 4/2000 | Igaki et al. | |
| 6,056,844 A | 5/2000 | Guiles et al. | |
| 6,080,177 A | 6/2000 | Igaki et al. | |
| 6,086,204 A | 7/2000 | Magnante | |
| 6,086,610 A | 7/2000 | Duerig et al. | |
| 6,139,536 A | 10/2000 | Mikus et al. | |
| 6,156,842 A | 12/2000 | Hoenig et al. | |
| 6,160,084 A | 12/2000 | Langer et al. | |
| 6,174,305 B1 | 1/2001 | Mikus et al. | |
| 6,179,878 B1 | 1/2001 | Duerig et al. | |
| 6,183,248 B1 | 2/2001 | Chisti et al. | |
| 6,200,335 B1 | 3/2001 | Igaki | |
| 6,217,609 B1 | 4/2001 | Haverkost | |
| 6,241,691 B1 | 6/2001 | Ferrera et al. | |
| 6,248,129 B1 * | 6/2001 | Froix | 623/1.42 |
| 6,283,992 B1 | 9/2001 | Hankh et al. | |
| 6,287,326 B1 | 9/2001 | Pecor | |
| 6,315,791 B1 | 11/2001 | Gingras et al. | |
| 6,323,459 B1 | 11/2001 | Maynard | |
| 6,348,065 B1 | 2/2002 | Brown et al. | |
| 6,364,904 B1 | 4/2002 | Smith | |
| 6,368,346 B1 | 4/2002 | Jadhav | |
| 6,388,043 B1 | 5/2002 | Langer et al. | |
| 6,395,038 B1 | 5/2002 | Schroeppel | |

| | | | |
|---|---|---|---|
| 6,406,493 B1 | 6/2002 | Tu et al. | |
| 6,413,272 B1 | 7/2002 | Igaki | |
| 6,413,273 B1 | 7/2002 | Baum et al. | |
| 6,416,545 B1 | 7/2002 | Mikus et al. | |
| 6,478,773 B1 | 11/2002 | Gandhi et al. | |
| 6,485,507 B1 | 11/2002 | Walak et al. | |
| 6,500,204 B1 | 12/2002 | Igaki | |
| 6,517,569 B2 | 2/2003 | Mikus et al. | |
| 6,517,570 B1 | 2/2003 | Lau et al. | |
| 6,530,950 B1 | 3/2003 | Alvarado et al. | |
| 6,538,089 B1 | 3/2003 | Samra et al. | |
| 6,596,818 B1 | 7/2003 | Zamore | |
| 6,632,242 B2 | 10/2003 | Igaki | |
| 6,679,605 B2 | 1/2004 | Zhou et al. | |
| 6,720,402 B2 | 4/2004 | Langer et al. | |
| RE38,653 E | 11/2004 | Igaki et al. | |
| 6,837,901 B2 | 1/2005 | Rabkin et al. | |
| 6,852,825 B2 | 2/2005 | Lendlein et al. | |
| 6,858,680 B2 | 2/2005 | Gunatillake et al. | |
| RE38,711 E | 3/2005 | Igaki et al. | |
| 7,037,288 B2 | 5/2006 | Rosenberg et al. | |
| 7,066,952 B2 | 6/2006 | Igaki | |
| 7,070,615 B1 | 7/2006 | Igaki | |
| 7,091,297 B2 | 8/2006 | Mather et al. | |
| 7,331,988 B2 | 2/2008 | Igaki | |
| 7,335,226 B2 | 2/2008 | Igaki | |
| 7,367,990 B2 | 5/2008 | Igaki | |
| 7,410,498 B2 | 8/2008 | Panhasi | |
| 7,473,273 B2 | 1/2009 | Campbell | |
| 7,498,042 B2 | 3/2009 | Igaki et al. | |
| 7,670,302 B2 | 3/2010 | Griffin et al. | |
| 8,070,793 B2 | 12/2011 | Igaki | |
| 2001/0029398 A1 | 10/2001 | Jadhav | |
| 2002/0007222 A1 | 1/2002 | Desai | |
| 2002/0015519 A1 | 2/2002 | Tokas et al. | |
| 2002/0055787 A1 | 5/2002 | Lennox et al. | |
| 2002/0137864 A1 | 9/2002 | Tong | |
| 2002/0151967 A1 | 10/2002 | Mikus et al. | |
| 2002/0156523 A1 | 10/2002 | Lau et al. | |
| 2002/0198584 A1 | 12/2002 | Unsworth et al. | |
| 2003/0033001 A1 | 2/2003 | Igaki | |
| 2003/0040803 A1 | 2/2003 | Rioux et al. | |
| 2003/0060530 A1 | 3/2003 | Topolkaraev et al. | |
| 2003/0060793 A1 | 3/2003 | Topolkaraev et al. | |
| 2003/0114777 A1 * | 6/2003 | Griffin et al. | 600/585 |
| 2003/0147046 A1 | 8/2003 | Shadduck | |
| 2003/0173702 A1 | 9/2003 | Igaki et al. | |
| 2003/0191276 A1 | 10/2003 | Lendlein et al. | |
| 2004/0014929 A1 | 1/2004 | Lendlein et al. | |
| 2004/0015187 A1 | 1/2004 | Leinlein et al. | |
| 2004/0015261 A1 | 1/2004 | Hoffman et al. | |
| 2004/0024143 A1 | 2/2004 | Lendlein et al. | |
| 2004/0030062 A1 | 2/2004 | Mather et al. | |
| 2004/0116641 A1 | 6/2004 | Mather et al. | |
| 2004/0122184 A1 | 6/2004 | Mather et al. | |
| 2004/0153025 A1 | 8/2004 | Seifert et al. | |
| 2004/0199242 A1 * | 10/2004 | Hong et al. | 623/1.16 |
| 2005/0010275 A1 | 1/2005 | Sahatjian et al. | |
| 2005/0245719 A1 | 11/2005 | Mather et al. | |
| 2005/0251249 A1 | 11/2005 | Sahatjian et al. | |
| 2006/0235501 A1 | 10/2006 | Igaki | |
| 2007/0260302 A1 | 11/2007 | Igaki | |

FOREIGN PATENT DOCUMENTS

| | | |
|---|---|---|
| DE | 102 28 120 A1 | 1/2004 |
| EP | 0 183 272 A2 | 6/1986 |
| EP | 0 183 372 A1 | 6/1986 |
| EP | 0 277 816 A1 | 8/1988 |
| EP | 0 324 946 A2 | 7/1989 |
| EP | 0 343 442 A2 | 11/1989 |
| EP | 0 368 274 A2 | 5/1990 |
| EP | 0 385 443 A2 | 9/1990 |
| EP | 0 404 004 A2 | 12/1990 |
| EP | 0 422 693 B1 | 6/1995 |
| EP | 1 00 958 A2 | 5/2000 |
| EP | 1 016 424 A1 | 7/2000 |
| JP | 612301051 | 10/1986 |
| JP | 62192440 | 8/1987 |

| | | |
|---|---|---|
| JP | 63145325 | 6/1988 |
| JP | 63179955 | 7/1988 |
| JP | 2274526 | 8/1990 |
| JP | 2232212 | 9/1990 |
| JP | 02-258845 | 10/1990 |
| JP | 2255830 | 10/1990 |
| JP | 2258817 | 10/1990 |
| JP | 3068610 | 3/1991 |
| JP | 3068611 | 3/1991 |
| JP | 04-109133 | 4/1992 |
| JP | 4100831 | 4/1992 |
| JP | 07-292040 | 11/1995 |
| JP | 8301952 | 11/1996 |
| JP | 9235329 | 9/1997 |
| JP | 1997309986 A | 12/1997 |
| JP | 10-001545 | 1/1998 |
| JP | 11-154420 | 8/1999 |
| JP | 11302493 | 11/1999 |
| JP | 2000119465 A | 4/2000 |
| JP | 2000319423 | 11/2000 |
| JP | 2005-065981 | 3/2005 |
| WO | WO 94/14890 | 7/1994 |
| WO | WO 95/26762 | 10/1995 |
| WO | WO 97/46633 | 12/1997 |
| WO | WO 99/42147 | 8/1999 |
| WO | WO 99/42528 | 8/1999 |
| WO | WO 99/42548 | 8/1999 |
| WO | WO 00/10485 | 3/2000 |
| WO | WO 00/15840 | 3/2000 |
| WO | WO 00/32131 | 6/2000 |
| WO | WO 00/33770 | 6/2000 |
| WO | WO 00/46262 | 8/2000 |
| WO | WO 00/71554 A2 | 11/2000 |
| WO | WO 00/78246 A2 | 12/2000 |
| WO | WO 01/07499 A1 | 2/2001 |
| WO | WO 01/56641 | 8/2001 |
| WO | WO 01/91822 A1 | 12/2001 |
| WO | WO 01/93783 A2 | 12/2001 |
| WO | WO 02/15951 A2 | 2/2002 |
| WO | WO 02/39875 A2 | 5/2002 |
| WO | WO 02/059170 | 8/2002 |
| WO | WO 02/060498 | 8/2002 |
| WO | WO 02/083786 A1 | 10/2002 |
| WO | WO 01/80936 A1 | 11/2002 |
| WO | WO 03/015840 A3 | 2/2003 |
| WO | WO 03/035743 A1 | 5/2003 |
| WO | 03/057075 | 7/2003 |
| WO | WO03/057075 | 7/2003 |
| WO | WO 03/084490 A1 | 10/2003 |
| WO | WO 03/084491 A1 | 10/2003 |
| WO | WO 03/088818 A2 | 10/2003 |
| WO | WO 03/093341 | 11/2003 |
| WO | WO 2004/006885 A2 | 1/2004 |
| WO | WO 2004/011525 | 2/2004 |
| WO | WO 2004/032799 A2 | 4/2004 |
| WO | WO 2004/033515 A2 | 4/2004 |
| WO | WO 2004/033539 A1 | 4/2004 |
| WO | WO 2004/033553 A1 | 4/2004 |
| WO | 2004/060428 | 7/2004 |
| WO | WO 2004/073690 A1 | 9/2004 |
| WO | WO 2004/090042 A1 | 10/2004 |
| WO | WO 2004/110515 A1 | 12/2004 |
| WO | WO 2005/009523 A1 | 2/2005 |
| WO | WO 2005/070988 A1 | 8/2005 |

OTHER PUBLICATIONS

"Hydroxyl Terminated Polybutadiene Resins and Derivtives—Poly bd® and Krasol®", Sartomer Product Bulletin, Sep. 2004.
"Silsesquioxanes, Bridging the Gap Between Polymers & Ceramics" ChemFiles vol. 1, No. 6, 2001.
"Suite of Shape-Memory Polymers", Chemical & Engineering, Feb. 5, 2001.
Bassi et al., "The Monoclinic Structure of Even Trans-Polyalkenamers", European Polymer Journal, vol. 3, pp. 339-352, 1967.
Bassi et al., "The Triclinic Structure of trans-Polyoctenamer", European Polymer Journal, vol. 4, pp. 123-132, 1968.
Bielawski et al., "Highly Efficient Ring-Opening Metathesis Polymerization (ROMP) Using New Ruthenium Catalysts Containing N-Heterocyclic Carbene Ligands", Angew. Chem. Int. Ed., 39, No. 16, pp. 2903-2906, 2000.
Bielawski et al., "Highly efficient syntheses of acetoxy- and hyroxy-terminated telechelic poly(butadiene)s using ruthenium catalysts containing N-heterocyclic ligands", Polymer, 42 , pp. 4939-4945, 2001.
Boochathum et al., "Vulcanization of Cis- and Trans-Polyisoprene and Their Blends: Cure Characteristics and Crosslink Distribution", European Polymer Journal 37, pp. 417-427, 2001.
Brochure, Degussa High Performance Polymers, The Rubber with Unique Properties, Vestenamer ©, Undated.
Calderon et al., "Melting Temperature of trans-Polyoctenamer", Journal of Polymer Science: Part A-2, vol. 5, pp. 1283-1292, 1967.
Chun et al., "Enhanced Dynamic Mechanical and Shape-Memory Properties of a Poly(ethylene terephthalate)-Poly(ethylene glycol) Copolymer Crosslinked by Maleic Anhydride", Journal of Applied Polymer Science, vol. 83, pp. 27-37, 2002.
Dinger, et al., "High Turnover Numbers with Ruthenium-Based Metathesis Catalysts" Advanced Synthesis Catalysis, vol. 344, pp. 671-677, 2002.
Du Prez et al., "Segmented Networks by Cationic Polymerization: Design and Applications" NATO Sci. Ser., Ser. E, pp. 75-98, 1999.
Fan et al., "Synthesis and Properties of Polyurethane Modified with Aminoethylaminopropyl Poly(Dimethyl siloxane)", Journal of Applied Polymer Science, vol. 74, pp. 2552-2558, 1999.
Fu et al., "Nanoscale Reinforcement of Polyhedral Oligomeric Silsesquioxane (POSS) in Polyurethane Elastomer", Polymer Int. 49, pp. 437-440, 2000.
Fu et al., "Structural Development During Deformation of Polyurethane Containing Polyhedral Oligomeric Silsesquioxanes (POSS) Molecules", Polymer 42, pp. 599-611, 2001.
Gajria et al., "Miscibility and Biodegradability of Blends of Poly(Lactic Acid) and Poly(Vinyl Acetate)", Polymer, vol. 37, pp. 437-444, 1996.
Ge et al., "Synthesis of Thermoplastic Polyurethanes Bearing Nanostructured Hard Segments: New Shape Memory Polymers" Polymer Program, Institute of Materials Science and Department of Engineering, UCONN, (Abstract, 2 pp.), Jul. 2003.
Goethals et al. "Poly(Vinyl Ethers) as Building Blocks for New Materials" Macromol. Symp., 132, pp. 57-64, 1998.
Gordon, "Applications of Shape Memory Polyurethanes", Proceedings of the First International Conference on Shape Memory and Superelastic Technologies, SMST International Committee, pp. 115-199, 1994.
Gupta et al., "Effect of solvent exposure on the Properties of hyroxy-terminated polybutadiene-based polyurethanes", Polym. Int. 52, pp. 938-948, 2003.
Irie, Shape Memory Polymers, Cambridge University Press: Cambridge, UK, pp. 203-219, 1998.
Ishii, "Shape Memory Resins", Trans-polyisoprene-based Shape Memory Resins, Zairyo Gijutsu, 7(6), Abstract only, 1 page, 1989.
Jeon et al., "Shape Memory and Nanostructure in Poly(norbornyl-POSS) Copolymers", Polymer International, 49, pp. 453-457, 2000.
Jeong et al., "Miscibility and Shape Memory Effect of Thermoplastic Polyurethane Blends with Phenoxy Resin", European Polymer Journal , 37, pp. 2245-2252, 2001.
Jeong et al., "Miscibility and Shape Memory Property of Poly(vinyl chloride)/Thermoplastic Polyurethane Blends", Journal of Materials Science, 36, pp. 5457-5463, 2001.
Kagami et al., "Shape Memory Behaviors of Crosslinked Copolymers Containing Stearyl Acrylate" Macromol. Rapid. Commun., 17(8), pp. 539-543, 1996.
Kaneko et al., "Shape Memory Gels with Multi-Stimuli-Responses", Proc. SPIE-Int. Soc. Opt. Eng., 3669, pp. 199-208, 1999.
Kannan et al., "Polyhedral Oligomeric Silisesquixoane Nanocomposites: The Next Generation Material for Biomedical Applications", Acc. Chem. Res., vol. 38, No. 11, pp. 879-884, 2005.
Kim et al., "Polyurethane Ionomers Having Shape Memory Effects", Polymer , vol. 39, No. 13, pp. 2803-2808, 1998.
Lendlein et al., "AB-Polymer Networks Based on Oligo(ε-caprolactone) Segments Showing Shape-Memory Properties" Proc. Natl. Acad. Sci., USA, 98(3), pp. 842-847, 2001.

Lendlein et al., "Biodegradable, Elastic Shape-Memory Polymers for Potential Biomedical Applications", Science, vol. 296, pp. 1673-1676, May 31, 2002.
Lendlein et al., "Shape-Memory Polymers", Angew. Chem. Int. Ed. 41, pp. 2034-2057, 2002.
Lin et al., "Study on Shape-Memory Behavior of Polyether-Based Polyurethanes. II. Influence of Soft-Segment Molecular Weight", Journal of Applied Polymer Science, vol. 69, pp. 1575-1586, 1998.
Lin et al., "Study on Shape-Memory Behavior of Polyether-Based Polyurethanes. I. Influence of the Hard-Segment Content", Journal of Applied Polymer Science, vol. 69, pp. 1563-1574, 1998.
Liu et al., "Shape Memory of Hydrogen-Bonded Polymer Network/Poly(ethylene glycol) Complexes", Chengdu Institute of Organic Chemistry, Chinese Academy of Sciences, 2003.
Liu et al., "Thermomechanical Characterization of a Novel Series of Shape Memory Polymers", SPE ANTEC Proceedings, 5 pages, 2002.
Liu, et al., "Chemically Cross-Linked Polycyloctene: Synthesis, Characterization and Shape Memory Behavior" Macromolecules, 35, pp. 9868-9874, 2002.
Mather et al., "Strain Recovery in Drawn POSS Hybrid Thermoplastics," XIIIth International Congress on Rheology, Cambridge, UK, 4, pp. 53-55, 2000.
Mather et al., "Strain Recovery in POSS Hybrid Thermoplastics," Polymer Preprints 41(1), pp. 528-529, 2000.
Mauler et al., "Functional Group Determination in Hydroxilated Polymer", Eur. Polym. J., vol. 31, No. 1, pp. 51-55, 1995.
Mauler et al., "Liquid-crystalline polyacrylate crosslinked with α, ω polyisoprene diacrylate segments", Polymer Bulletin, 41, pp. 291-297, 1998.
Nakayama, K., "Properties and Applications of Shape-Memory Polymers", International Polymer Science and Technology, 18, T/43-48, 1991.
Oh et al., "Dynamic Mechanical Properties of Carbon Black Filled Trans-polyoctenamer Vulcanizates", Abstract Only, (Oct. 19, 1985).
Paul Starck, "Dynamic Mechanical Thermal Analysis on Ziegler-Natta and Metallocene Type Ethylene Copolymers", Eur. Poly. J. vol. 33, No. 3, pp. 339-348, 1997.
Ramanathan et al., "Polyurethane elastomers", Polymer Data Handbook, pp. 874-877, 1999.
Ramanathan et al., "Polyurethane urea", Polymer Data Handbook, pp. 878-881, 1999.
Ramanathan et al., "Polyurethane", Polymer Data Handbook, pp. 870-873, 1999.
Reyntjens et al., "Polymer Networks Containing Crystallizable Poly(octadecyl vinyl ether) Segments for Shape-Memory Materials", Macromol. Rapid. Commun., 20(5), pp. 251-255, 1999.
Rousseau et al., "Shape Memory Effect Exhibited by Smectic-C Liquid Crystalline Elastomers" J. Am. Chem. Soc., 125, pp. 15300-15301, 2003.
Sarbu et al., "Synthesis of Hydroxy-Telechelic Poly(methyl acrylate) and Polystyrene by Atom Transfer Radical Coupling", Macromolecules, 37, pp. 9694-9700, 2004.
Schneider et al., "Crystallinity of trans-Polyoctenamer: Characterization and Influence of Sample History", Journal of Molecular Catalysis, 46, pp. 395-403, 1988.
Schwab et al., "Synthesis and Applications of RuC12(=CHR')(PR3)2: The Influence of the Alkylidene Moiety on Metathesis Activity", J. Am. Chem. Soc., 118, pp. 100-110, 1996.
Schwab et al., "Hybrid Nanoreinforced Polyurethanes Based on Polyhedral Oligomeric Silsesquioxanes(Poss)", ACS Polymeric Materials Science and Engineering, Fall Meeting, 1997, vol. 77, pp. 549-550.
Schwabb et al., "Polyhedral Oligomeric Sil silsesquioxanes (POSS): Silicon Based Monomers and Their Use in the Preparation of Hybrid Polyurethanes", Mat. Res. Soc. Symp. Proc., vol. 519, pp. 21-27, 1998.
Sung et al., "Properties of Segmented Poly(urethaneureas) Based on 2,4-Toluene Diisocyanate. 1. Thermal Transitions, X-ray Studies, and Comparison with Segmented Poly(urethanes)", Macromolecules, 13, pp. 111-116, 1980.
Valimaa et al., "Viscoelastic memory and self-expansion of self-reinforced bioabsorbable stents", Biomaterials, 23, pp. 3575-3582, 2002.
Van Humbeeck, "Shape Memory Alloys: A Material and a Technology", Advanced Engineering Materials, vol. 3, No. 11, pp. 837-850, 2001.
Wache et al., "Development of a polymer stent with shape memory effect as a drug delivery system", Journal of Materials Science: Materials in Medicine, 14, 109-112, (2003).
Wei et al., "Shape-Memory Materials and Hybrid Composites for Smart Systems", Journal of Materials Science 33, pp. 3743-3762, 1998.
Woojin Lee, "Polymer Gel Based Actuator: Dynamic model of gel for real time control", Massachuetts Institute of Technology, Department of Mechanical Engineering, May 3, 1996.
Yeh et al., "Radiation-Induced Crosslinking: Effect on Structure of Polyethylene", Colloid & Polymer Sci. 263, pp. 109-115, 1985.
Yoshida et al., "Development and Application of Shape-Memory Polymer Gel (Part 1)—Synthesis and Processing of Shape-Memory Polymer Gel", Hokkaidoritsu Kogyo Shikenjo Hokoku, 298 Abstract Only, 1 page, 1999.
Zhu et al., "Shape-Memory Effects of Radiation Crosslinked Poly(ε-caprolactone)", Journal of Applied Polymer Science, vol. 90, pp. 1589-1595, 2003.
"Cross-link" definition, Wikipedia (http://en.wikipedia.org/wiki/Cross-link), 6 pages, Nov. 20, 2013.
"POSS® (Polyhedral Oligomeric Silsesquioxane) Molecules from READE," READE—Your Higher Technology Specialty Chemicals Resource, READ SuperSite Search, (http://www.reade.com/products/37-polymeric-powders/646-polyhedral-oligomeric-silsequioxane-molecular-silica-poss-molecules-poss-molecular-silicas-poss-chemicals-poss-monomers-poss-silanols-heatabrasion-resistant-paints-and-coatings-mechanical-property-m), published Feb. 1, 2001, 3 pages.

* cited by examiner

*Primary Examiner* — Darwin Erezo
*Assistant Examiner* — Sidharth Kapoor
(74) *Attorney, Agent, or Firm* — Fish & Richardson P.C.

(57) ABSTRACT

A medical device includes a balloon catheter having an expandable member, e.g., an inflatable balloon, at its distal end and a stent or other endoprosthesis. The stent is, for example, an apertured tubular member formed of a polymer and is assembled about the balloon. The stent has an initial diameter for delivery into the body and can be expanded to a larger diameter by inflating the balloon.

20 Claims, 27 Drawing Sheets

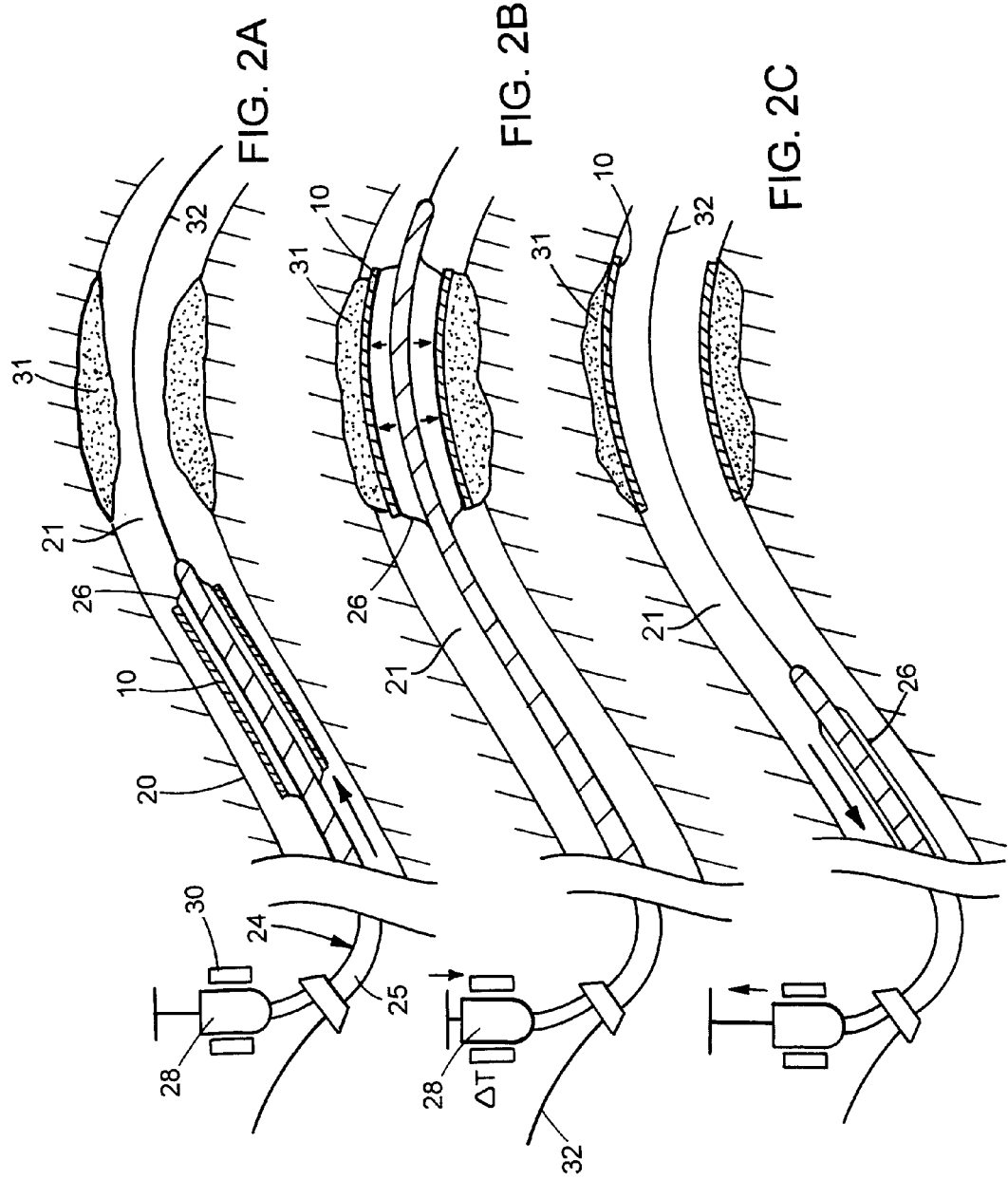

DSC scan (second scan) of polyurethanes with different PEG:POSS
Molar ratio A) 1:3 B) 1:4 C) 1:6 D) 1:8

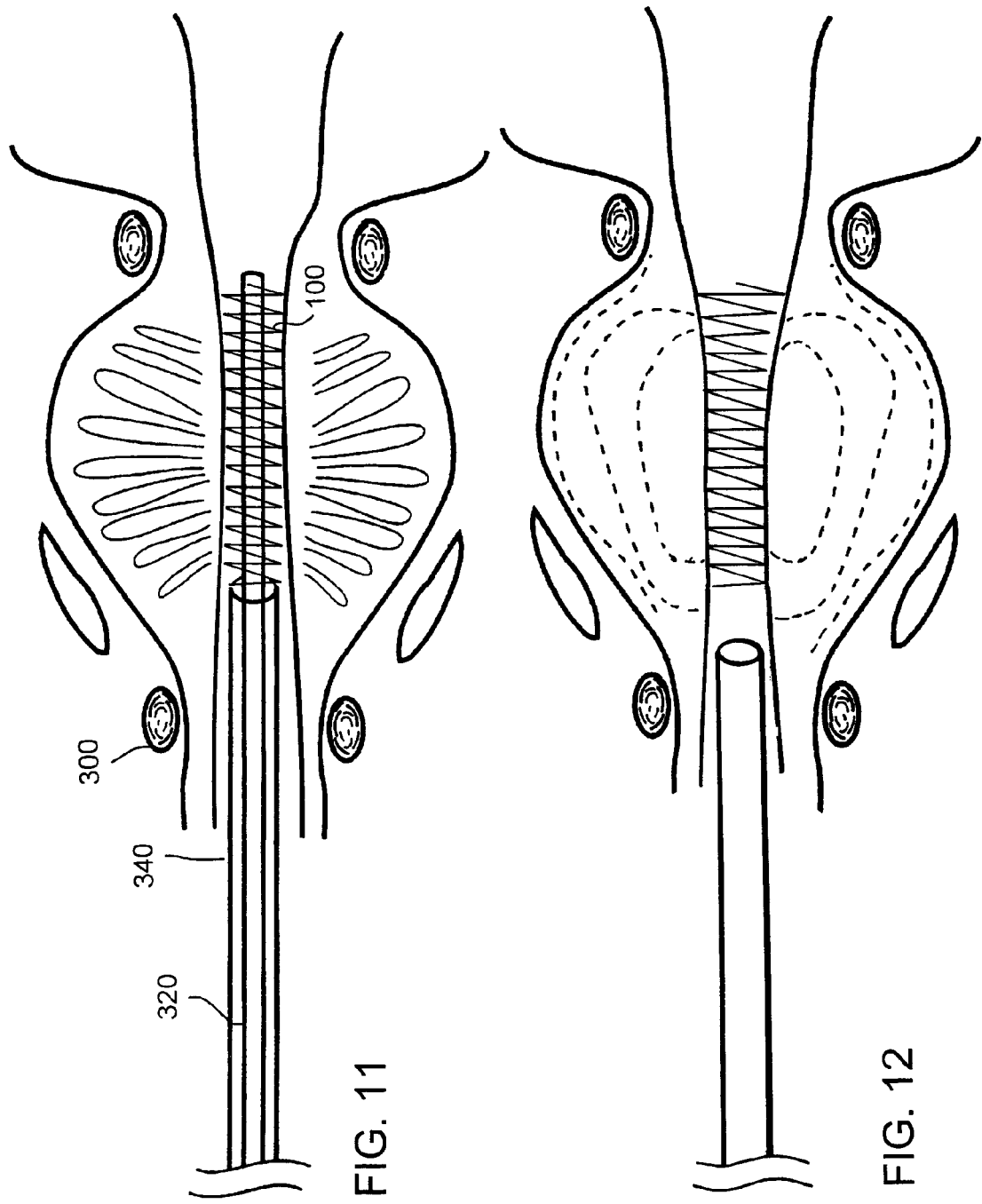

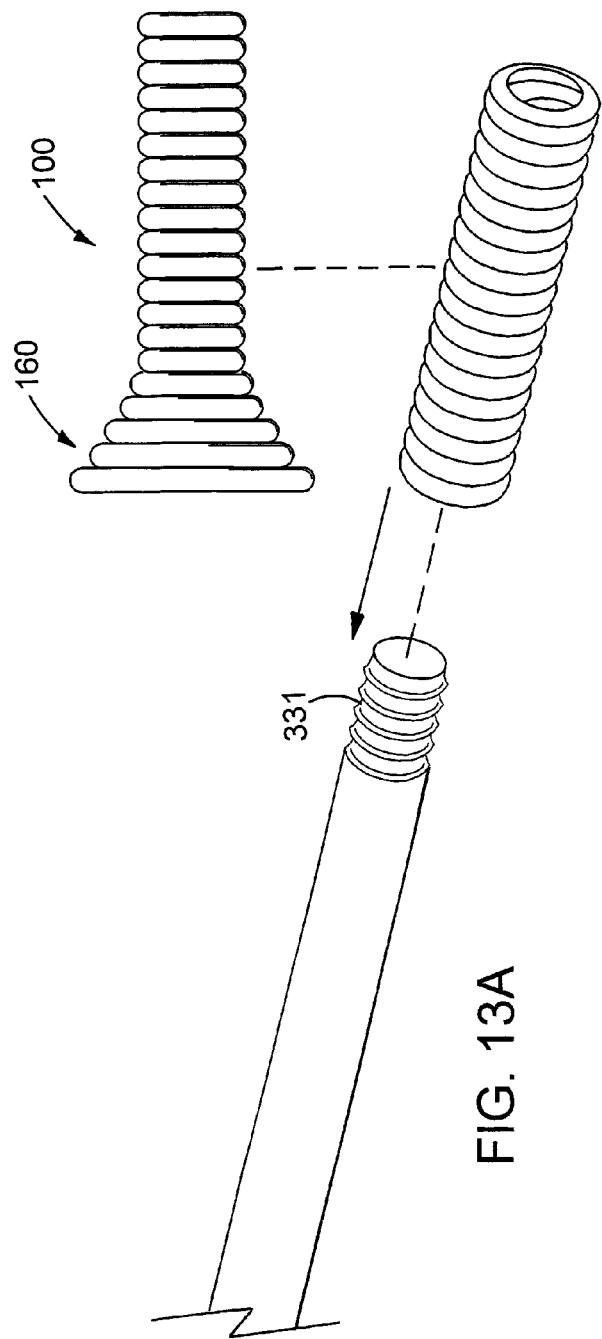
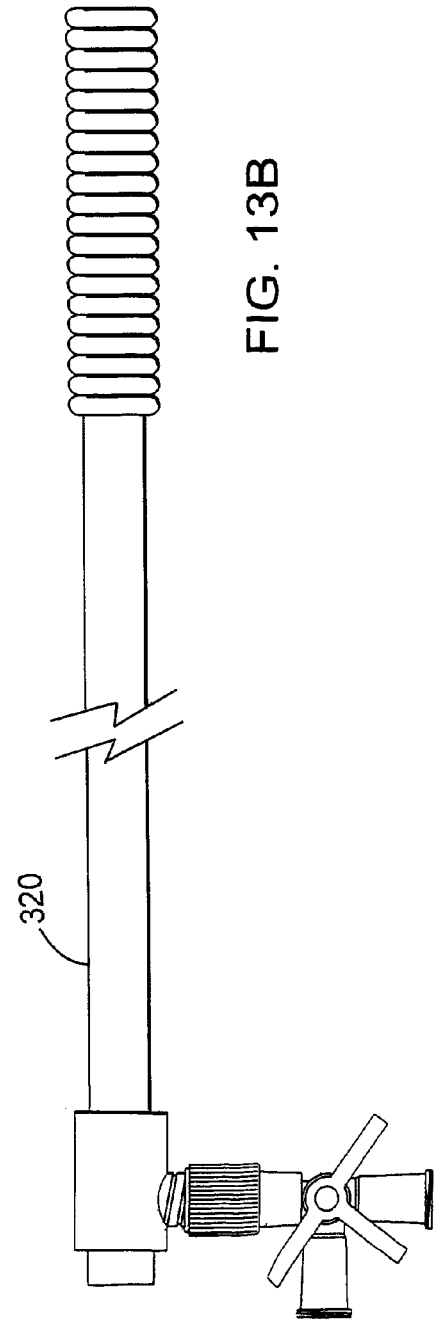
FIG. 13A
FIG. 13B

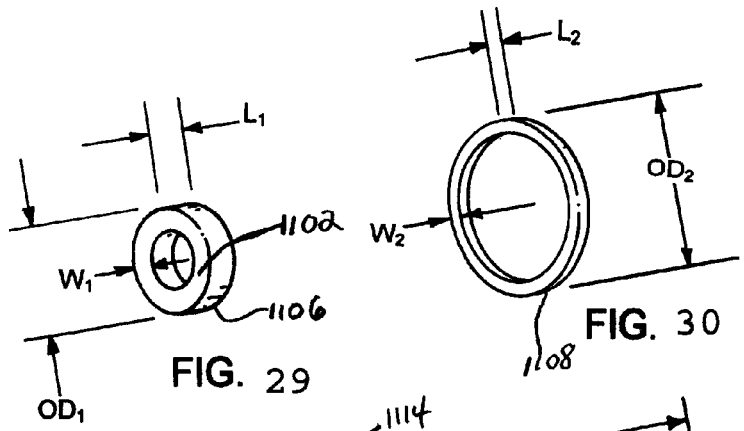
FIG. 29
FIG. 30
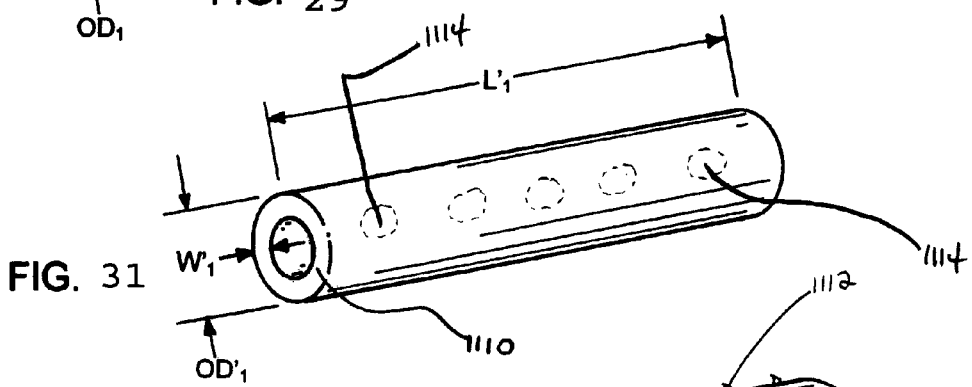
FIG. 31
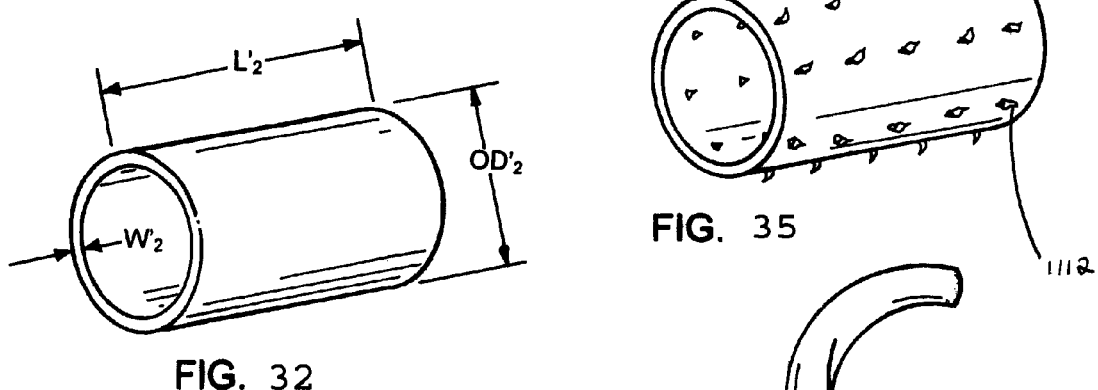
FIG. 32
FIG. 35
FIG. 33
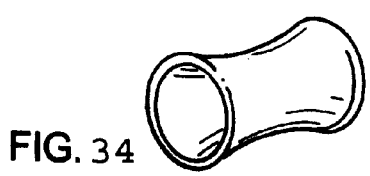
FIG. 34

US 8,784,465 B2

IMPLANTABLE MEDICAL DEVICES

CROSS REFERENCE TO RELATED APPLICATIONS

This application is a divisional of, and claims benefit of priority from U.S. patent application Ser. No. 12/880,483, filed Sep. 13, 2010, which is a divisional of U.S. patent application Ser. No. 10/958,435, filed Oct. 5, 2004, now U.S. Pat. No. 7,794,494, which is a continuation-in-part of, and claims benefit of priority from U.S. patent application Ser. No. 10/683,314, filed Oct. 10, 2003, now abandoned, which claims the benefit of priority from U.S. Provisional Patent Application Ser. No. 60/418,023, filed Oct. 11, 2002, U.S. Provisional Patent Application Ser. No. 60/488,323, filed Jul. 18, 2003, U.S. Provisional Patent Application Ser. No. 60/419,506, filed Oct. 18, 2002, U.S. Provisional Patent Application Ser. No. 60/466,401, filed Apr. 29, 2003, and U.S. Provisional Patent Application Ser. No. 60/488,590, filed Jul. 18, 2003, the contents of each application above is hereby incorporated by reference herein in its entirety.

TECHNICAL FIELD

This invention relates to implantable medical devices and methods of delivering the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

Prostate enlargement, also known as benign prostate hyperplasia or benign prostate hypertrophy, is a common affliction among older men. The condition involves swelling of the prostate. The prostate surrounds the urethra, or urinary tract, and enlargement of the prostate may restrict passage of urine from the bladder towards the urethra. Benign prostate hyperplasia is uncomfortable because it makes urination difficult or impossible. The condition is also dangerous because it can lead to infection of the bladder and kidneys.

Prostate enlargement can be treated with surgery known as resection. Resection can be accomplished by cutting away a large portion of the prostate gland. Prostate enlargement can also be treated with heat treatment, cold treatment, or ablation.

Sometimes a restricted urethra can be treated with a prostatic stent to support the urethra and keep it open despite pressure from the enlarged prostate. A prostatic stent may be implanted permanently or as an interim solution.

SUMMARY

The invention relates to implantable medical devices, for example, a stent including a polymer.

In one aspect, the invention features a medical device. The medical device includes a balloon catheter having an expandable member, e.g., an inflatable balloon, at its distal end and a stent or other endoprosthesis. The stent is an apertured tubular member formed of a polymer and is assembled about the balloon. The stent has an initial diameter for delivery into the body and can be expanded to a larger diameter by inflating the balloon. The polymer does not flow substantially during expansion and substantial stress relaxation or creep does not occur so that the geometry of the stent is maintained.

In another aspect, a tubular endoprosthesis including a polymer body is provided and delivered into a body lumen. The endoprosthesis is expanded in the body lumen under conditions of expanding pressure and temperature so that the wall thickness of the polymer body is substantially maintained.

In another aspect, a polymer tube is formed to a first, large diameter. An aperture pattern is cut into the tube wall. The polymer is crosslinked or crystallized. The polymer tube is deformed to a second, small diameter. The polymer tube is expanded in a body lumen to a diameter larger than the second diameter by application of pressure and heat.

In another aspect, a polymer tube is formed to a first, small diameter. An aperture pattern is provided in the tube wall. The polymer is crystallized or crosslinked. The tube is expanded in a body lumen by application of pressure and heat.

In another aspect, an implantable medical apparatus includes an element operable for movement within the body by mechanical force applied to the element. The element includes a polymer having a melt or glass transition temperature in the range above body temperature to about 50° C. or 60° C. and exhibiting a plateau in a plot of storage modulus as a function of temperature at melt or glass transition. In embodiments, the element is a stent. The stent may be generally a tubular body that includes an apertured wall. The stent may be operable for expansion from a first, smaller diameter to a second larger diameter for implantation in a lumen. The thickness of the stent wall varies by about 1% or less between the first and second diameter.

In another aspect, the invention features a medical device including a polymer having a melt or glass transition temperature above body temperature and exhibiting an approximate plateau in a plot of storage modulus as a function of temperature at melt or glass transition. The melt or glass transition temperature may be, for example, above about 37° C. The medical device may undergo a triggerable event at about the plateau. The triggerable event may be, for example, a change in the flexibility, a change in the porosity, a change in the coefficient of friction or a change in the surface roughness. The medical device may be, for example, a stent that has a portion that has a collapsed position that can be reverted to an expanded position by a trigger subsequent to insertion into the body.

Aspects may include one or more of the following features. The polymer body, optionally, includes apertures. The polymer body has a ratio of aperture open area to wall area of about 0.5 or more or 0.7 or more. The endoprosthesis is expanded by simultaneously applying an expanding pressure and heat to the endoprosthesis. The polymer body is heated above the melt or glass transition temperature of polymer in the polymer body. The polymer body is elastomeric at the melt or glass transition temperature. The polymer is elastomeric at body temperature. The polymer is crystalline. The polymer is crosslinked. The polymer is radiation crosslinked. The melt or glass transition temperature is about 40 to 50° C. The melt or glass transition temperature has a transition range of about 5° C. or less. The polymer exhibits a plateau in the melt or glass transition range in a plot of storage modulus as a function of temperature. The polymer body includes a drug, radiopaque agent or magnetic heating agent. The polymer is a shape memory polymer, e.g. capable of remembering a smaller diameter configuration after expansion. The polymer is, for example, polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/poly-methyl-methacrylate (PMMA), polyurethanes, styrene-butadiene copolymers, polyethylene, trans-isoprene, blends of polycaprolactone and n-butylacrylate, PVC, e.g., plasticized PVC, and blends thereof. An expansion pressure of about 1 atm or more is applied. The endoprosthesis is delivered on a catheter. The endoprosthesis is delivered to a site of occlusion and the site is simultaneously dilated while expanding the endoprosthesis. The endoprosthesis is delivered to a site of lumen curvature and the endoprosthesis is expanded at the site. The endoprosthesis is delivered to a vascular lumen. The endoprosthesis is delivered adjacent (into) the prostate.

Aspects may include one or more of the following. A heat applicator applies heat to the stent during inflation of the balloon to expand the balloon to the expanded diameter. The polymer has a melt or glass transition temperature in the range of about 40 to 50° C. and a modulus at the melt or glass transition temperature sufficient to maintain the stent geometry or under application of pressure and/or heat. The polymer exhibits a plateau in the storage modulus in the range of melt or glass transition temperatures. The stent has a wall thickness of about 0.005 to 5 mm. The stent has an initial unexpanded inner diameter in the range of about 1 mm to 5 mm. The stent has an expanded inner diameter of about 1 mm to 20 mm. The stent may be expandable to about 100% or 400% or more of the initial inner diameter. An example of a coronary stent has an initial inner diameter of about 2 mm, and expanded inner diameter of about 4 mm and the wall thickness is about 0.005 mm to 0.1 mm. The stent can be in the form of a tube including aperture areas provided in the tube. The aperture are in the shape of elongate slots, e.g., when the stent is in the small diameter condition. The apertures have a dimension of about 1 mm or less in the small diameter condition. The apertures are in the shape of diamond-like openings, e.g. when the stent is in an expanded condition. The stent can be a wire-form formed of one or more filaments configured to generally define a tube.

Embodiments may include one or more of the following advantages. A balloon expandable stent made of a polymer can be provided that maintains the integrity of the stent geometry on expansion and heating. Maintenance of stent geometry is desirable since geometry affects, for example, the resistance to compression in the body and a predictable geometry is important to avoid irregular surfaces, kinking, or extensions of material into the body lumen which can interfere with the flow of body fluid. The polymers can be elastomers that have melting or glass transitions at temperatures safe for use in the body and exhibit elastomeric properties at both the melted or glass transition stage and the solid or crystalline phase. The stent body exhibits high resistance to inward compressive forces when the polymer is in the solid or crystalline phase. The elastomeric nature of the polymer in the melted or glass state enhances the ability to maintain geometry as the stent is expanded. For example, the polymer exhibits minimal flow during expansion and the thickness of the stent remains substantially constant. Elastomeric properties in the crystalline or solid state enhance the ability to conform to torturous curvature in narrow body lumens. High compression resistance allows the stent to maintain the body lumen open and resist occluding forces such as elastic recoil or the growth of thrombus from the vessel wall.

In another aspect, the invention features a polymeric stent having a portion that has a collapsed position that can be reverted to an expanded position by heating above a first temperature subsequent to insertion of the stent into a cavity or lumen. The stent may be in the form, for example, of a coiled elongated element (for example, a strand, a tape or a flattened tube). The stent may be further heated to a second temperature that is higher than the first temperature and removed as a substantially uncoiled element. When the stent is in the form, for example, of a coiled elongated flattened tube, the flattened tube may include a central opening that includes a medicament that can be released by the inserted stent. In some implementations, the medicament is compounded into the plastic or is a coating on the plastic. In some implementations, the portion is at an end of the stent and the portion is flared or stepped. In other implementations, the portion includes less than 50% of the length of the stent.

In another aspect, the invention features a polymeric stent in the form of a coiled elongated element, and having a portion that has a collapsed position that can be reverted to an expanded position by heating above a first temperature subsequent to insertion of the stent into a cavity or lumen. When the stent is heated to a second temperature higher than the first temperature, the modulus of the element lowers sufficiently that the stent can be removed from the cavity or lumen as a substantially uncoiled element.

In yet another aspect, the invention features a method of treating a non-vascular cavity or lumen. The method includes inserting a polymeric stent having a portion in a collapsed position that can be reverted, by heating, to an expanded position. Following insertion, the stent is heated sufficiently to revert the portion in the collapsed position to the expanded position. The method may further include heating the stent having the portion in the expanded position sufficiently to soften the stent, and removing the softened stent from the cavity or lumen.

The stent may be, for example, a coiled elongated element (for example, a rod, a tape or flattened tube) and the heating of the stent prior to removal allows the stent to be removed in a substantially uncoiled state. This method provides ease of removal, for example, for removing prostatic stents that have been inserted on an interim basis. The heating may be performed, for example, on a delivery tube.

In some embodiments, the portion of the stent is at the end of the stent and may be flared when in the expanded position. In other embodiments, for example, the portion of the stent is not at an end of the stent.

In still another aspect, the invention features a polymeric stent including metal particles. A portion of the stent has a collapsed position that can be reverted to an expanded position by heating. The heating may be performed using inductive heating to revert the portion in the collapsed position to the expanded position.

In another aspect, the invention features a stent having an exterior surface that includes a plurality of protruding elements that extend outwardly from the surface. The protruding elements may be useful in helping the stent retain its position, for example, after insertion into the prostatic urethra.

In some embodiments, the protruding elements are formed of monofilament. The monofilament may include a plurality of constrictions along its length.

In some implementations, the stent is a polymeric stent and the stent has a portion that has a collapsed position that can be reverted to an expanded position by heating above a first temperature subsequent to insertion of the stent into a cavity or lumen.

In another aspect, the invention features an implantable endoprothesis including a tubular member that includes a polymeric material. The tubular member has a wall having a first transverse dimension and a first longitudinal length, measured when at the first transverse dimension, sized for delivery into a lumen. Upon exposure to an elevated temperature, the tubular member can be expanded to a second transverse dimension that is at least about fifty percent larger than the first transverse dimension within the lumen, the first and second transverse dimensions being measured from an outer surface of the wall of the tubular member. The tubular member also has a second longitudinal length, measured when at the second transverse dimension. After expansion from the first transverse dimension to the second transverse dimension, the second longitudinal length decreases by less than about fifty percent, measured relative to the first longitudinal length.

In some implementations, the tubular member has a wall thickness, measured from an inner surface of the wall to the outer surface of the wall, and the wall thickness decreases by greater than about twenty percent, e.g., greater than about thirty percent, greater than about fifty percent, greater than about seventy-five percent, or greater than eighty-five percent, after expansion from the first transverse dimension to the second transverse dimension.

In some embodiments, after expansion from the first transverse dimension to the second transverse dimension that is at least about forty percent larger than the first transverse dimension, e.g., seventy-five percent larger than the first transverse dimension, the second longitudinal length decreases by less than about twenty percent, measured relative to the first longitudinal length.

The tubular member can be, for example, approximately circular in transverse cross-section, or the tubular member can have other transverse shapes, e.g., non-circular, e.g., elliptical.

In some embodiments, the polymeric material has a softening temperature from about 40° C. to about 60° C., e.g., 45, 50, 55, or 58° C. The polymeric material can be cross-linked, non-cross-linked, a shape memory polymer, or a non-shape memory polymer. In some instances, the polymeric material is, for example, polycyclooctene (PCO), a styrenic elastomer, a styrenic block copolymer, a styrene-butadiene rubber, a polyolefin, trans-isoprene, or blends of these materials. The polymeric material can include a filler, e.g., a radio-opaque agent, e.g., bismuth carbonate, barium sulfate, or mixtures of these materials. Other fillers includes, for example, a thermal conductor, e.g., a boron nitride, other ceramics, or a metal.

In some implementations, the tubular member is, for example, substantially straight before it is expanded. In specific embodiments, the tubular member is curved after it is expanded and/or the outer surface of the wall of the tubular member includes a protruding element that extends outwardly from the outer surface after the tubular member is expanded.

In some embodiments, the wall of the tubular member includes at least one aperture defined therein.

In some implementations, the plastic has a elastic modulus of greater than about 50,000 psi, e.g., greater than about 75,000, greater than about 150,000, greater than about 250,000, or greater than about 500,000 psi.

In another aspect, the invention features a method of treating a patient. The method includes placing the endoprosthesis just discussed on a delivery system. The delivery system then is used to deliver the endoprosthesis a lumen, e.g., a pulmonary lumen, an esophageal lumen, a biliary lumen, an enteral lumen, a ureteral lumen, and a urethral lumen. The endoprosthesis then is heated and expanded within the lumen. In a specific implementation, the delivery system includes a balloon catheter.

The details of one or more embodiments of the invention are set forth in the accompanying drawings and the description below. Other features, and advantages of the invention will be apparent from the description and drawings and from the claims.

DESCRIPTION OF DRAWINGS

FIGS. 2A-2C illustrate delivery of a stent into a body lumen.

FIG. 11 is a cross-sectional view illustrating delivery of a stent to the prostatic urethra.

FIG. 12 is a cross-sectional view of a prostatic stent deployed in the urethra.

FIG. 13A-13B are side views of an alternative delivery system.

FIGS. 29 and 30 are perspective views of a tubular stent in an unexpanded state and in an expanded state, respectively.

FIGS. 31 and 32 are perspective views of an elongated, tubular stent in an unexpanded state and in an expanded state, respectively.

FIG. 33 is a perspective view of a curved tubular stent in an expanded state.

FIG. 34 is a perspective view of a tubular stent in an expanded state that has flared ends.

FIG. 35 is a perspective view of an elongated tubular stent having an outer surface that includes a plurality of projections.

DETAILED DESCRIPTION

Figure 1A:
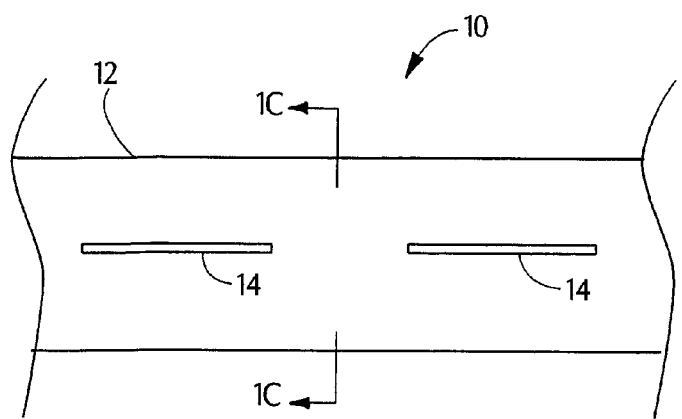
FIGS. 1A and 1B are side views of a portion of a stent in a small diameter and expanded condition, respectively.
Figure 1C:
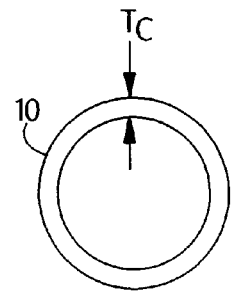
FIGS. 1C and 1D are cross-sectional views of a portion of a stent in a small diameter and expanded condition, respectively.
Figure 1B:
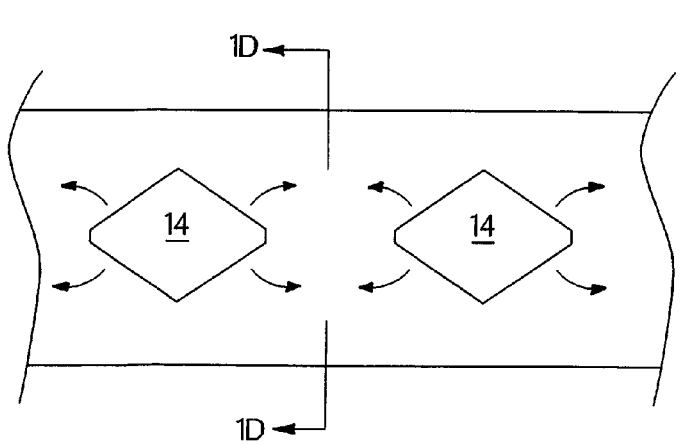
Figure 1D:
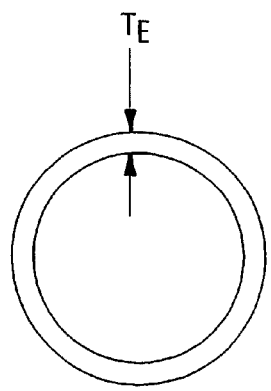

Referring to FIGS. 1A and 1B, a stent 10 includes a polymer body 12 generally defining a tube. The stent includes open areas 14. Referring particularly to FIG. 1A, in a small diameter condition, such as for delivery to a treatment site in the body, the open areas are relatively small and defined as slots cut through the wall of the stent. Referring particularly to FIG. 1B, in the expanded condition, the slots are widened to diamond-like shapes. The expansion mechanism of the stent utilizes a deformation (arrows) of the wall material about the open areas. As illustrated, the expansion results in a generally regular, symmetric, geometric pattern that resists and distributes inward compression of the stent by forces imposed by the lumen wall. Referring as well to FIGS. 1B and 1D, the wall thickness T of the stent does not substantially change upon expansion from the small diameter collapsed ($T_C$) condition to the expanded condition ($T_E$)($T_C=T_E$). The polymer does not substantially flow or thin out on expansion, so that a reliable expansion geometry and wall thickness can be achieved. Other stent constructions are suitable. For example, filament-form stents in which filaments of polymer material are arranged to define a generally tubular structure can be used. Open areas are defined between the filaments. An example of a stent design including helical filaments is provided in Wallsten, U.S. Pat. No. 4,655,771. Suitable aperture wall designs are also described in Palmaz U.S. Pat. No. 4,733,665. Another suitable arrangement is exemplified by the Express stent, commercially available from Boston Scientific, Natick, Mass.

Referring to FIGS. 2A-2C, the delivery of a stent into the body is illustrated. The stent is delivered utilizing a catheter 24, which includes a catheter body 25 that carries a balloon 26 at its distal end. At the proximal end, the catheter includes an inflation apparatus 28 such as a syringe or pump apparatus which can be used to inject and circulate inflation fluid into the catheter, where it is directed by a lumen to the interior of the balloon so that the balloon can be inflated. In addition, the inflation apparatus can include a heating apparatus 30, to heat the inflation fluid directed to the balloon. The catheter is delivered into a vessel 20 including body lumen 21 in a patient to the site of an obstruction 31 typically utilizing a guidewire 32. The guidewire 32 extends through a lumen within the body 25 of the catheter.

Referring particularly to FIGS. 2A and 2B, the stent 10 is positioned over the inflatable balloon 26. Referring particularly to FIG. 2A for delivery into the body, the balloon is initially in a small diameter deflated condition. The stent is in a small diameter condition over the balloon. Referring particularly to FIG. 2B, when the treatment site is reached, the balloon is inflated by actuating the inflation apparatus 28. The inflation fluid is heated to heat the polymer body of the stent 10. By providing outward radial force while heating the stent, the stent is expanded into contact with body lumen 21. The stent can be expanded simultaneously with the widening of the obstructed region. After expansion to the desired diameter, the temperature of the inflation fluid is typically decreased to reverse the softening of the stent body 10. Referring particularly to FIG. 2C, after the temperature of the stent has been reduced in this manner, it remains implanted in the vessel to resist vessel recoil and reduce restenosis after the balloon is deflated and the catheter is removed from the body.

Suitable polymers include those that maintain stent geometry under expansion conditions, allowing for intricate stent geometries such as apertured tubes having high open area to wall ratios. At temperatures above body temperature and under conditions of radial expanding pressure, the stent can be expanded without fracture or substantial irreversible stress relaxation or creep. Typically, the stent is heated to or above the melt or glass transition temperature during expansion. In this condition, the polymer is in a softened state. In this state, the polymer can be predictably deformed, typically about aperture regions during expansion. In addition, the soft condition permits proper apposition of the stent to the lumen wall without kinking and without damage due to excessive stiffness, which could straighten the lumen from its native curvature and lead to dissections or other trauma. After the stent is fully expanded and cooled, the polymer substantially sets in the proper apposition, e.g. about a native curvature. Excessive recoil of the stent to a linear configuration is avoided, reducing trauma about the vessel. At the same time, the polymer can have some elastomeric properties in the cooled, hardened state so that the stent can flex with natural vessel motion. After cooling, the stent exhibits sufficient resistance to inward radial force to reduce restenosis due to, e.g., lumen wall recoil. The polymer has sufficient strength so that the stent wall can be kept relatively thin while resisting restenosis from lumen wall forces.

Suitable polymers include elastomers that are crosslinked, crystalline, or amorphous, e.g. plasticized PVC, e.g., PVC plasticized with a monomeric plasticizer, e.g., a phthalate, or a polymeric plasticizer. The crosslinked and/or crystalline nature is sufficient to resist excessive creep or stress relaxation when the polymer is heated and expanded. The polymer can be crosslinked so that it exhibits the desired elastomeric properties but not crosslinked to the degree that it becomes excessively brittle. Too little crosslinking does not establish sufficient resistance to flow during heating and expansion to maintain stent geometry. In addition, crosslinking can be adjusted to adjust the melt or glass transition temperature and transition temperature range. A narrow melt transition range is desirable, e.g. 5° C. or 10° C. or less. Crosslinking can be achieved by application of radiation such as e-beam, UV, gamma, x-ray radiation or by heat-activated chemical crosslinking techniques. Chemical crosslinking agents include peroxides, such as benzoyl peroxide or dicumyl peroxide (DCP), and azo compounds, such as 2,2'-azobis(2,4-dimethyl valeronitrile) or 2,2'-azobis[N-(2-propenyl)-2-methylpropionamide]. Radiation techniques provide the advantage that the polymer typically does not have to be substantially heated to achieve crosslinking. An intricate aperture pattern provided in a stent precursor tube can be maintained and heat-induced flow of pre-crosslinked polymer can be avoided. For gamma radiation, an exposure of about 50-300, e.g. 250 kilograys typically provides sufficient crosslinking Melting and crystallization temperatures are measured using a differential scanning calorimetry.

Figure 3:
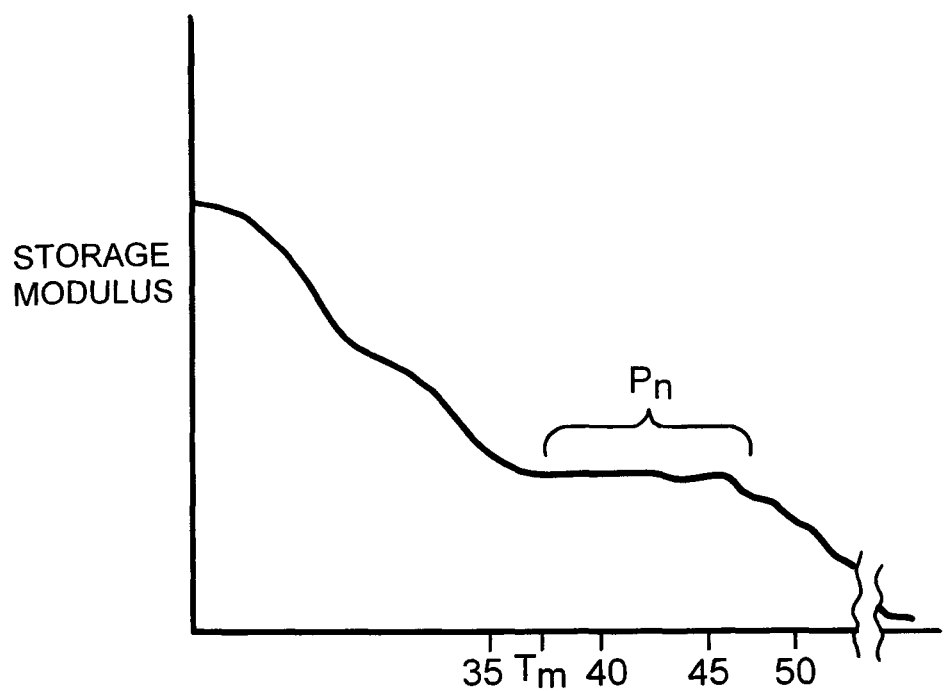
FIG. 3 is a plot of storage modulus as a function of temperature.

The polymer can have elastomeric properties in the melted or softened state. Elastomeric properties at melt or glass transition can be investigated by measuring the modulus of elasticity or storage modulus as a function of temperature and determining the elastomeric nature of the material in the desired expansion temperature range. Referring to FIG. 3, a plot of storage modulus as a function of temperature is provided. Storage modulus decreases as the material is heated. At the melt or glass transition, a plateau "P" is typically consistent with an elastomeric nature. At much higher temperatures, the modulus drops off more quickly, indicating a material which could flow under pressure. To determine storage modulus, a dynamic mechanical analyzer (Perkin Elmer) can be used. Dynamic mechanical analysis was carried out in tensile mode at an operating frequency of 1 Hz, a static force of 10 mN, and oscillation amplitude of 5 μm (approximately 0.1% strain) and an automatic tension setting of 125%. Temperature ramps were conducted at 4° C./minute over the range −100° C. to 100° C.

Figure 3A:
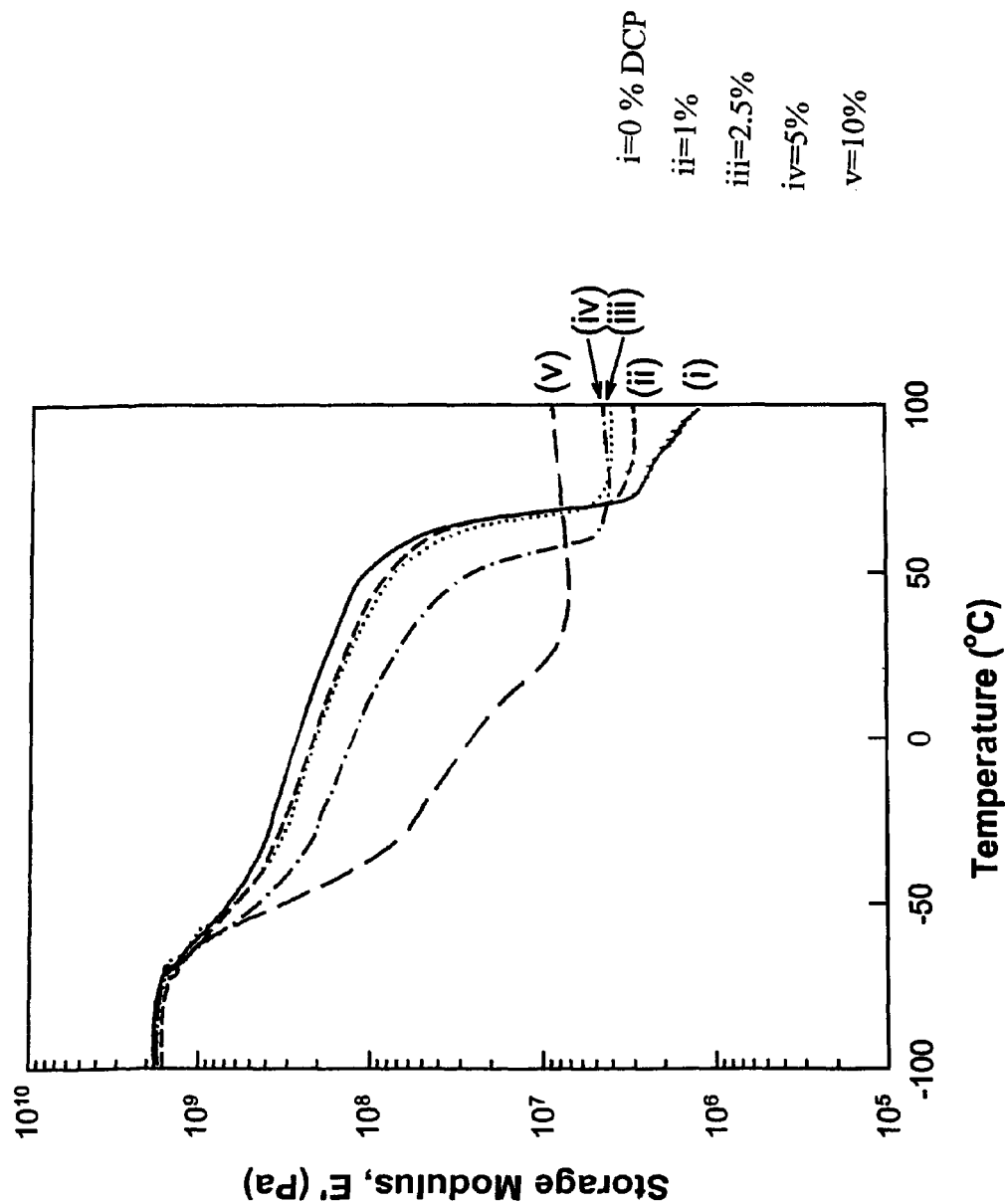
FIG. 3A is a plot of storage modulus as a function of temperature for samples of PCO with varying degrees of crosslinking
Figure 3B:
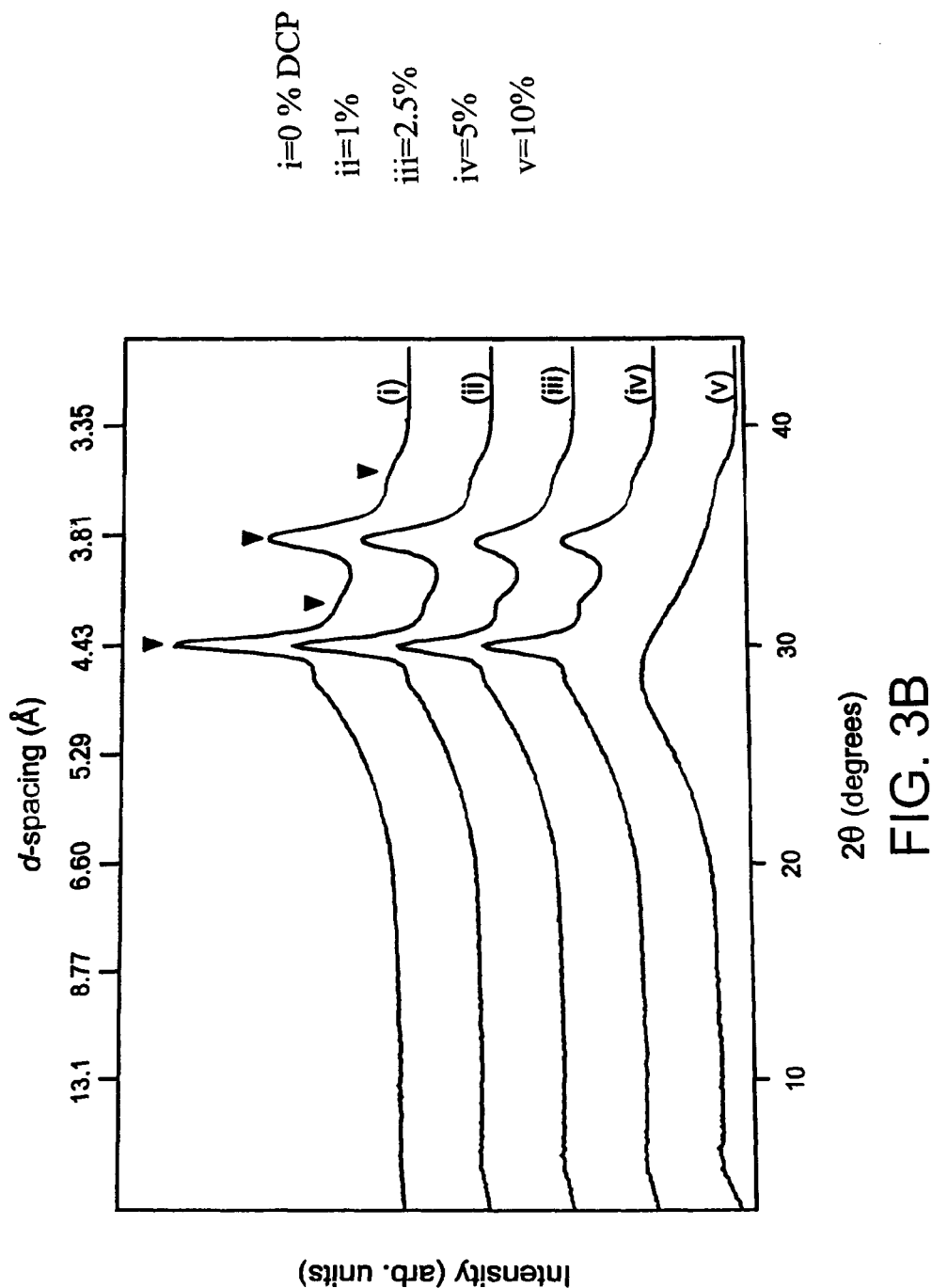
FIG. 3B is a WAXS 2θ plot for samples of PCO with varying degrees of crosslinking.

Chemically crosslinking PCO also has a direct impact on the thermomechanical properties, e.g. modulus versus temperature, through the establishment of a permanent network and indirectly through morphological transitions. Revealing such effects by the use of DMA, FIG. 3A shows plots of the tensile storage modulus (E') versus temperature for cured PCOs prepared with varying amounts of DCP. All of the PCO samples are characterized by a solid-like storage modulus (about 1.7 GPa) for temperatures below T=−70° C. with this modulus value being invariant to the crosslinking density. For temperatures above T=−70° C., the apparent onset of $T_g$ in the PCO samples, E' begins to decrease gradually to a level that is dependent on crosslink density, but spanning 0.05 to 0.5 GPa. The decrease in the modulus with crosslinking in this temperature region can be understood from the results of the DSC and wide angle x-ray scattering (WAXS), FIG. 3B, that showed crosslinking reduces the degree of crystallinity of PCO. It is to be expected that the crystalline phase will function as both the fixing mechanism for shape memory and a means of controlling room temperature modulus over a full order of magnitude. For temperatures nearing T=62° C., close to the melting temperature measured by DSC, the storage modulus of neat PCO begins to decrease sharply to about 2 MPa at the completion of melting at 71° C. As found with DSC, this transition temperature is observed mechanically to decrease with increasing degree of crosslinking. For temperatures greater than $T_m$, the modulus of neat PCO, trace (i), continues to decrease to a point where the material flows like a viscous liquid, not showing a persistent rubbery plateau (FIG. 3). This feature hampers the applicability of neat PCO for use as a shape memory polymer due to an inability to be deformed as a rubber above $T_m$ without rapid stress relaxation. On the other hand, cured PCO, which contains just 1% peroxide, represented by trace (ii), will allow significant shape memory effects owing to its persistent rubbery plateau above 72° C. As the amount of peroxide increases, the rubbery plateau modulus increases, allowing for enhanced mechanical energy storage, but the transition temperature and the steepness of the transition decrease. In the case of PCO with 10% DCP, shown as trace (v) in FIG. 3A, the thermomechanical response that is observed is inconducive to shape memory effects as the fixing (crystallization) temperature is lower than room temperature so that shape fixing would require subambient cooling and the temporary shape would be expected to drift via partial melting. In addition, the melting transition is too broad for dramatic strain recovery to be expected.

Suitable polymers include elastomers that are typically crosslinked and/or crystalline and exhibit melt or glass transitions at temperatures that are above body temperature and safe for use in the body, e.g. at about 40 to 50° C. Suitable polymers can have an elastic modulus of about 60,000 or 70,000 psi or more at 25° C. (ASTM D638M). Such polymers may have a variety of room temperature moduli, from rigid glassy materials having storage moduli of several GPa to compliant rubbers with moduli as low as tens of MPa. Moreover, the moduli may tuned over the range 0.5<E<10 MPa, as dictated by the end application. Suitable polymers include polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene (particularly, crosslinked polyethylene), transisoprene, block copolymers of polyethylene terephthalate (PET), blends of polycaprolactone and n-butylacrylate, and PVC, e.g., plasticized PVC, e.g., PVC plasticized with a monomeric plasticizer, e.g., a phthalate, or a polymeric plasticizer. A suitable PVAc/PVDF tube is formed by compounding 60-80 parts (by weight) PVAc (B-100, mw 500,000, ChemPoint, Cleveland, Ohio) with 40 to 20 parts PVDF (Grade 1010, Solvay Fluoropolymers, Houston, Tex.). The PVAc/PVDF is a crystalline material that can be utilized with or without crosslinking.

The polymer body can be made of mixtures of polymers or multiple polymer layers. The polymer forming the stent body can be compounded to include a drug, which elutes from the polymer, or radiopaque material. The structural polymer body can be coated with other polymers to carry drug or control drug delivery from the structural polymer. The polymer body can also exhibit shape memory properties. This feature of the polymer can be used in combination with the expansion properties discussed above. For example, the polymer can be configured to remember an enlarged or reduced diameter configuration. For example, the stent can be delivered into the body, and expanded by a combination of heat and radial pressure as described above. After a time, the stent can be retrieved by reheating the stent. In this case, the heating causes the stent to revert its small diameter condition. The remembered stent diameter is less than the vessel diameter and the stent can be more easily removed from the vessel. Such an application might be useful, for example, for a stent delivered into the prostate where removal and replacement is desirable.

Figure 4:
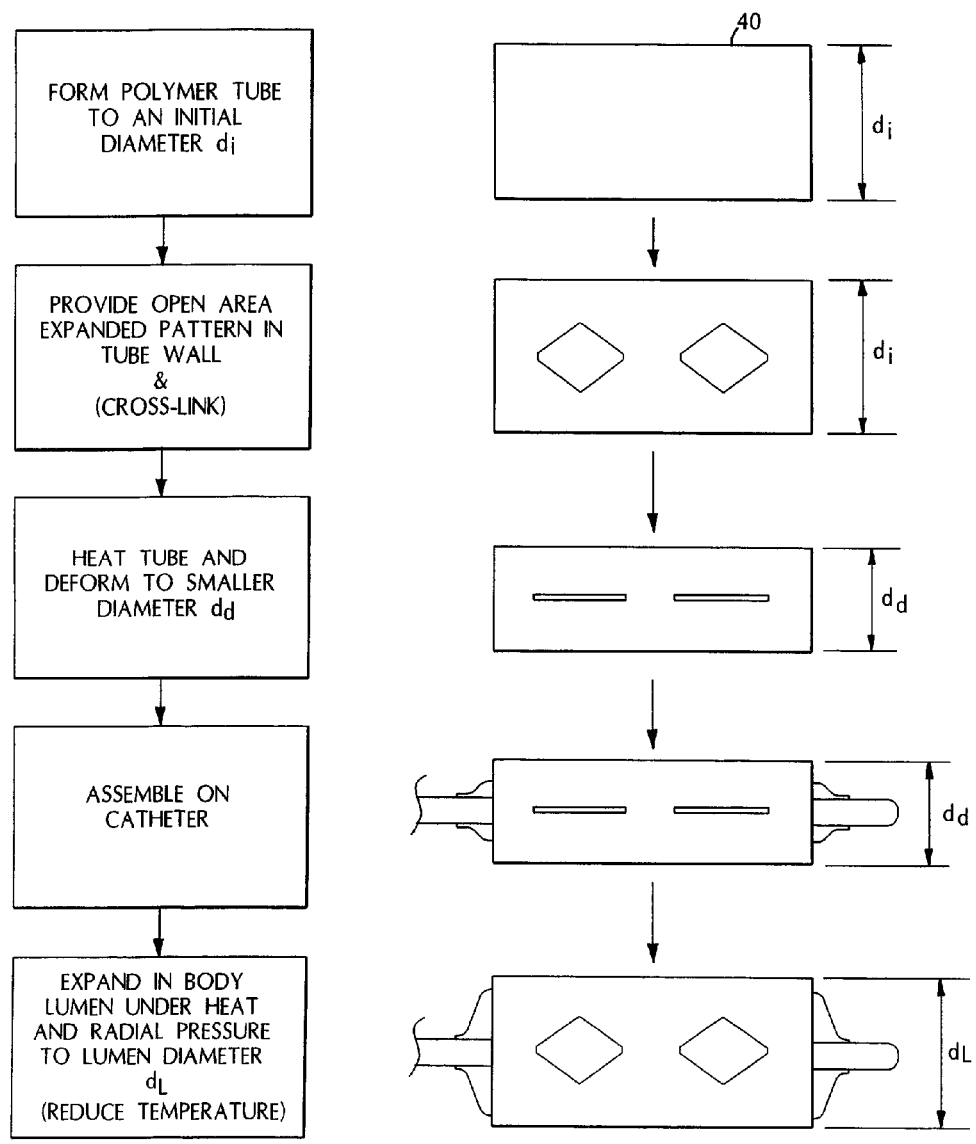
FIG. 4 illustrates manufacture and use of a stent.
Figure 5:
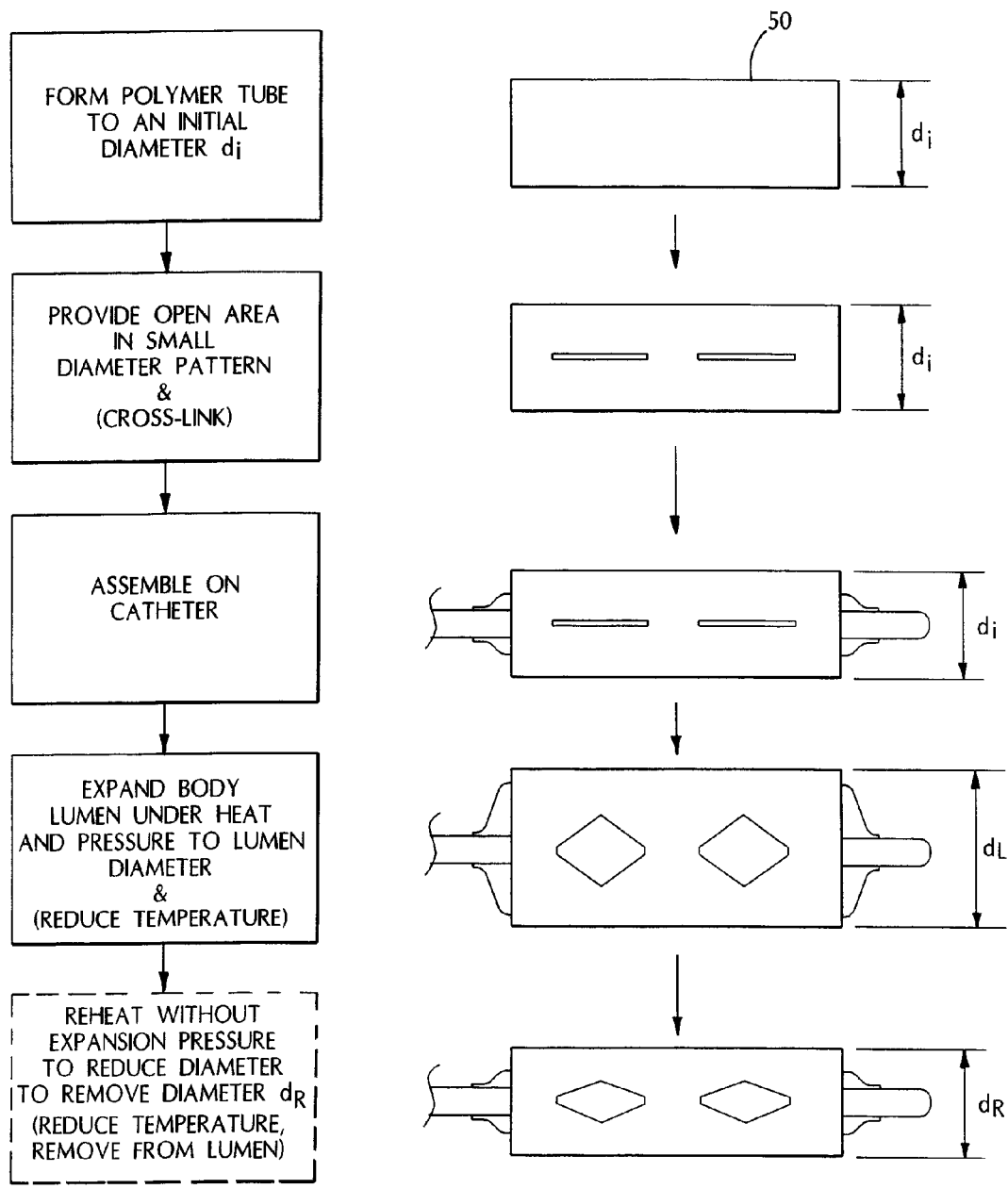
FIG. 5 illustrates manufacture and use of a stent.

Referring to FIGS. 4 and 5, manufacture and use of the stent is illustrated. Referring particularly to FIG. 4, in a first step, a polymer tube 40 is constructed by extrusion or molding a suitable polymer to an initial diameter di which in the same or greater than the target lumen diameter. (For stents made of polymer strands, the strands can be formed by extrusion, followed by arranging the strands into a tube, e.g. by weaving or knitting.) The tube wall is then cut to provide a pattern of open areas in a desirable geometric pattern, e.g. by laser cutting. The polymer can be recrystallized or crosslinked, if necessary. Next, the tube is heated typically near or above the melt or glass transition and mechanically deformed to a small diameter, suitable for delivery. The tube is cooled, e.g. to room temperature. The tube is assembled onto a catheter, delivered into the body, and expanded by application of heat, to the melt or glass transition, while inflating the balloon as discussed above. (If the polymer has shape memory properties, the polymer tends to expand upon heating to a larger, remembered diameter.

Referring particularly to FIG. 5, a polymer tube 50 is constructed to an initial diameter di, smaller than the vessel diameter. The tube wall is cut to provide an open area in a desirable pattern so that when the stent is expanded, a compression-resistant geometry will result. The polymer is recrystallized or crosslinked, if necessary. The tube is assembled in a catheter, delivered into the body, and expanded by heating to the melt or glass transition temperature while inflating the balloon to provide an outward radial expansion, as discussed above. If the polymer has shape memory properties, the stent can be subsequently re-heated so it reverts back to its remembered small diameter configuration and removed from the body.

In particular embodiments, the stent can have an expanded inner diameter of about 2 to about 20 mm. The initial inner diameter can be in the range of about 1 to about 3 mm. The wall thickness is in the range of about 0.005 mm to 20 mm. The wall thickness variation between delivery and expanded states is within about 10%, 5% or 1% or less. The ratio of the open area to the wall area in the expanded state is about 0.5 to 0.7 or more. (The tube wall area is the area of the tube defined by polymer. The open area is the open area defined by the apertures.) A particular stent for coronary use has an initial diameter of about 2 mm, an expanded diameter of about 4 mm, and a wall thickness of about 0.005 mm to 0.1 mm. The stent can be used for various applications including coronary, neuro, carotid, peripheral vasculature, ureteral, and prostate lumens. The stent is particularly useful where the lumen path is highly curved or irregular.

The catheter can be, e.g. an angioplasty balloon catheter with a relatively non-distendable inflating balloon suitable for expansion of occluded regions of a vascular lumen. The balloon may include a polymer such as PET, which has a burst pressure of about 1.5 to 5 atm or more. The stent can be heated by heating the balloon inflation fluid. The balloon inflation fluid can be heated by e.g., heating the fluid delivery device outside the body using e.g., resistive heating tape. Alternatively, the catheter can carry a heating device. For example, a resistive heater or RF heater can be provided in the interior of the balloon. A heated balloon catheter is described in Abele et al. U.S. Pat. No. 5,496,311 and U.S. Pat. No. 4,955,377. Vessel heating as described in the '311 can be used in combination with stent delivery as discussed herein. Alternatively, the stent can be heated directly. For example, the polymer can be compounded to include a material, such as magnetic particles, which are susceptible to heating by magnetic effects, such as hysteresis effects. A magnetic field can be imposed on the stent body by a source on a catheter or outside the body. Particles are available as the Smartbond System from Triton Systems, Inc., Chelmsford, Mass. Heating by magnetic effects is discussed in U.S. Pat. No. 6,056,844. The stent can also be heated during delivery without applying expansion force to soften the stent, improving its flexibility and thus improving delivery to a treatment site through a tortuous vessel path.

EXAMPLE

A polycyclooctene polymer (Vistenemer 8012 pellets, mw 90,000, Degussa, N.J.) is melt processed in an extruder to produce a tube having dimensions of about 0.118 inch O.D. and 0.070 inch I.D. (wall thickness about 0.024 inch). The tube is cut to a length of about 4 cm. The tube is subject to UV excimer laser ablation cutting to provide an aperture pattern of rectangular slots having a width of about 0.2 mm and a length of about 8 mm. Beam energy and pulse rate are selected to avoid substantial heating or melting of the polymer. The polymer can be compounded with about 10% $TiO_2$ (T8141, Dupont) to enhance absorption of laser radiation. A suitable pattern is consistent with the Express stent (commercially available from Boston Scientific, Natick, Mass.). (Alternatively, a pattern as described in Palmaz U.S. Pat. No. 4,733,665 can be used.) The tube is heated to a temperature below its melt point, e.g., to about 39 to 40° C. in a water bath and expanded by balloon catheter to a diameter of about 5 mm and positioned on a mandrel (PTFE tube) to maintain the expanded shape and diameter. The tube is then cooled to room temperature. The polymer is then crosslinked by e-beam radiation at 250 K Grays (Steris Isomedics Services, Northborough, Mass.). Crosslinking fixes the stent in the condition. (The crosslinked PCO has an elastic (Youngs) modulus of about 74945 psi at about 25° C. (ASTM D638M)). The stent is heated to the polymer melt temperature, about 45° C. and collapsed over a deflated balloon (diameter of about 2 mm) with a 4 mm inflated maximum diameter and 2 cm length. (A suitable balloon catheter is a 75 cm Meditech UltraThin Catheter, available from Boston Scientific, Natick, Mass.). The balloon and stent are immersed in a water bath of about 42 to 45° C. and water the same temperature is used to inflate the balloon. The stent is expanded to about 4 mm diameter (ID) at an inflation pressure of about 1 to 1.5 atm (measured at the delivery syringe). After expansion, the heating is discontinued and the balloon and inflation fluid allowed to cool to body temperature (while the balloon remains inflated). Alternatively, a cooled contrast fluid can be circulated to the balloon. The stent exhibits no visible reduction in wall thickness or irregular flow of polymer into the stent open areas. In addition, in the heated, expanded state, the stent can be bent around a mandrel of about 0.75 cm radius without kinking. After the stent is cooled, it maintains the curved form.

Figure 6:
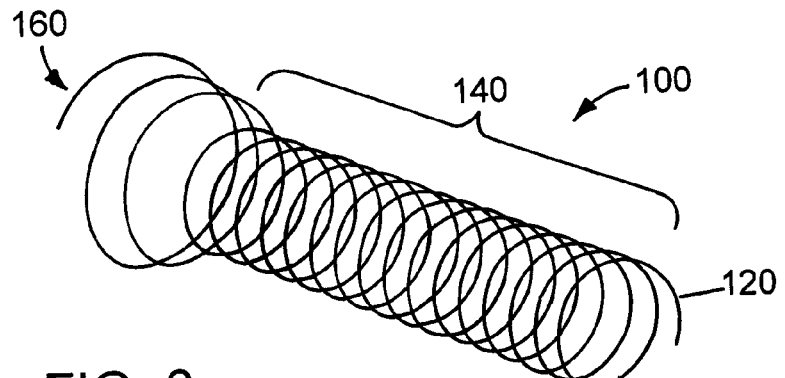
FIG. 6 is a perspective view of a stent with an end in an expanded position.
Figure 7:
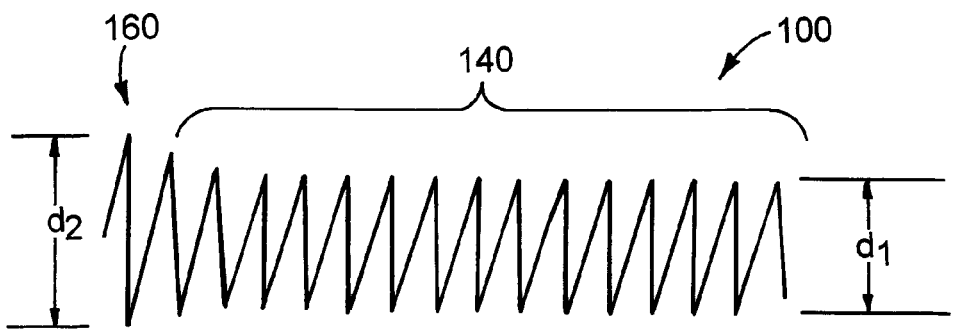
FIG. 7 is a side view of the stent shown in FIG. 6.
Figure 8:
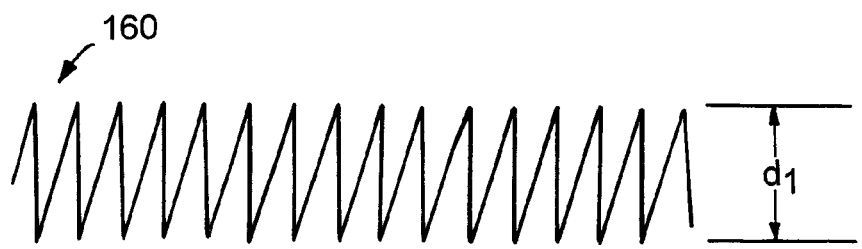
FIG. 8 is a side view of the stent shown in FIG. 6 with the end in a collapsed position.

Referring to FIGS. 6-8, stent 100 includes a coiled rod 120 composed of a polymer. Stent 100 includes an elongated portion 140 having a general diameter $d_1$ and an end portion 160 having a maximum diameter $d_2$. General diameter $d_1$, for example, may be between about 3 mm and about 25 mm, more preferably between about 6 mm and about 14 mm, and maximum diameter $d_2$, for example, may be between about 7 mm and about 30 mm, more preferably between about 10 mm and about 17 mm. When stent 100 is designed, for example, for insertion into a urethra, the stent may have an overall length, for example, of between about 3 mm and about 15 mm, preferably between about 6 mm and 10 mm, and end portion 160 may have a length, for example, of from about 3 mm to about 15 mm, preferably from about 5 mm to about 10 mm. End portion 160 is in a flared position. Referring to FIG.

8, stent 100 is shown with end portion 160 in a collapsed position that can be reverted with heating to the expanded position shown in FIGS. 6 and 7.

Generally, the portion of the stent in the collapsed position that can be reverted to the expanded position is, for example, greater than 5%, 10%, or even 25% of the overall length L of the stent, and less than 80% or 65% of the overall length L of the stent. For example, the of the overall length L of the stent may be between 10% and 65% of the overall length L of the stent.

The polymers preferably are cross-linked and/or crystalline elastomers that have melt or glass transition temperatures that are above body temperature, for example, greater than 45° C. or 55° C. The degree of cross-linking can be used to adjust, for example, the melt or glass transition temperature, and range, of the polymer. The polymer preferably has a relatively narrow, for example, less that 5° C. or 10° C., melt or glass transition temperature range.

The polymer preferably has elastomer properties in its melted or softened state. Preferred polymers have an elastic modulus, for example, of about 60,000 psi or 70,000 psi or more at 25° C. (ASTM D638).

Examples of polymers include polynorbornene and copolymers of polynorbornene, blends of polynorbornene with KRATON® (thermoplastic elastomer) and polyethylene, styrenic block copolymer elastomers (e.g., styrene-butadiene), polymethylmethacrylate (PMMA), polyethylene, polyurethane, polyisoprene, polycaprolactone and copolymers of polycaprolactone, polylactic acid (PLA) and copolymers of polylactic acid, polyglycolic acid (PGA) and copolymers of polyglycolic acid, copolymers of PLA and PGA, polyenes, nylons, polycyclooctene (PCO), polyvinyl acetate (PVAc), polyvinylidene fluoride (PVDF), blends of polyvinyl acetate/polyvinylidine fluoride (PVAc/PVDF), blends of polymethylmethacrylate/polyvinyl acetate/polyvinylidine fluoride (PVAc/PVDF/PMMA) and polyvinylchloride (PVC).

In some embodiments, the polymers above are also useful for the stents of FIGS. 1, 4 and 5.

Particular polyurethanes are made by reacting (A) a polyol, (B) a chain extender dihydroxyl-terminated POSS and (C) a diisocyanate, where POSS stands for a polyhedral oligomeric silsesquioxane diol. The polyol (A) can be polyethylene glycol (PEG), polycaprolactone (PCL), polycyclooctene (PCO), trans-1,4 butadiene, transisoprene, polynorbornene diol and polymethacrylate copolymer, the chain extender (B) can be TMP cyclopentyldiol-POSS, TMP cyclohexyldiol-POSS, TMP isobutyldiol-POSS, trans-cyclohexanediolcyclohexane-POSS, or transcyclohexanediolisobutyl-POSS and the diisocyanate (C) can be selected from a large number of diisocyanates and is preferably 4,4' diphenyl methylene diisocyanate (MDI). Other diisocyanates (C) that are suitable for use in the synthesis of hybrid polyurethane SMPs include: toluene-2,4-diisocyanate (TDI), toluene-2,6diisocyanate, hexamethylene-1,6-diisocyanate (HDI), 4,4' diphenylmethane diisocyanate (MDI), isophorone diisocyanate (IPDI), and hydrogenate 4,4'-diphenylmethane diisocyanate (H12MDI).

Figure 8A:
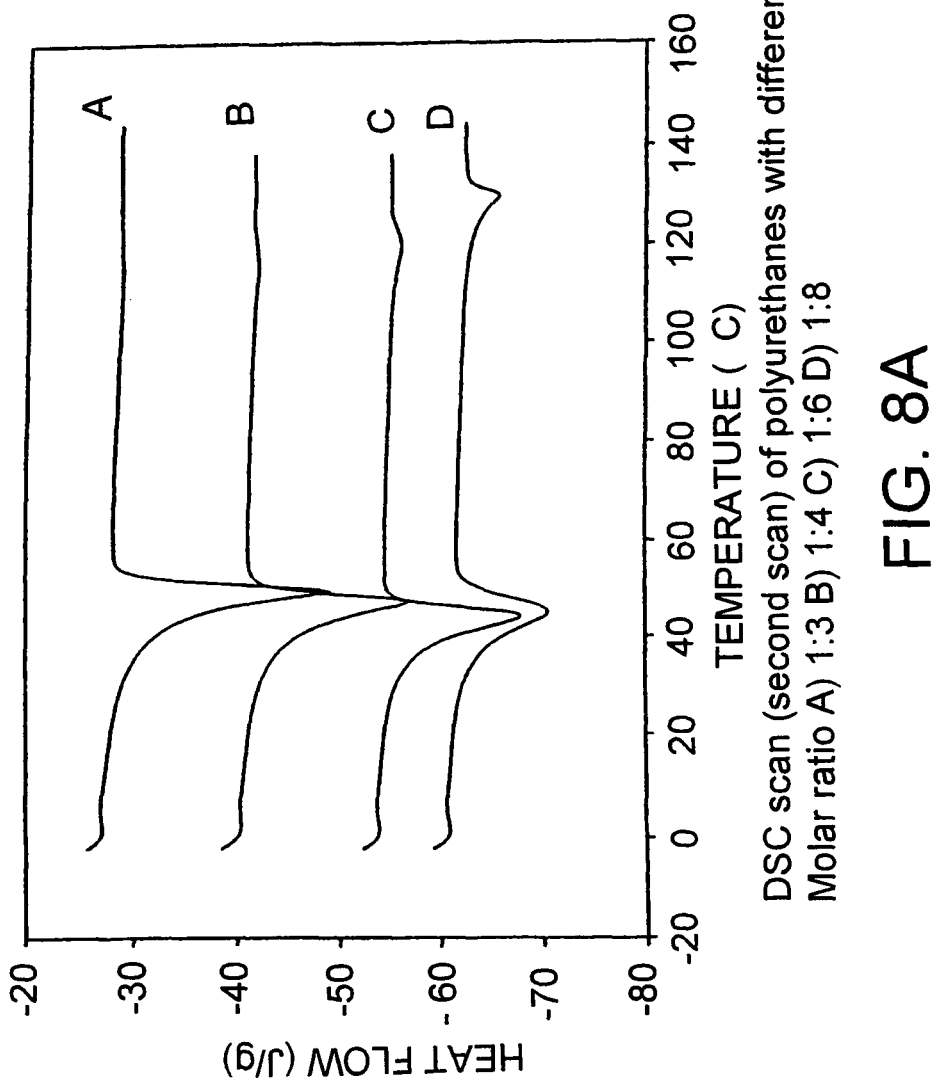
FIG. 8A is a graph of heat flow as a function of temperature for several POSS polyurethanes.
Figure 8B:
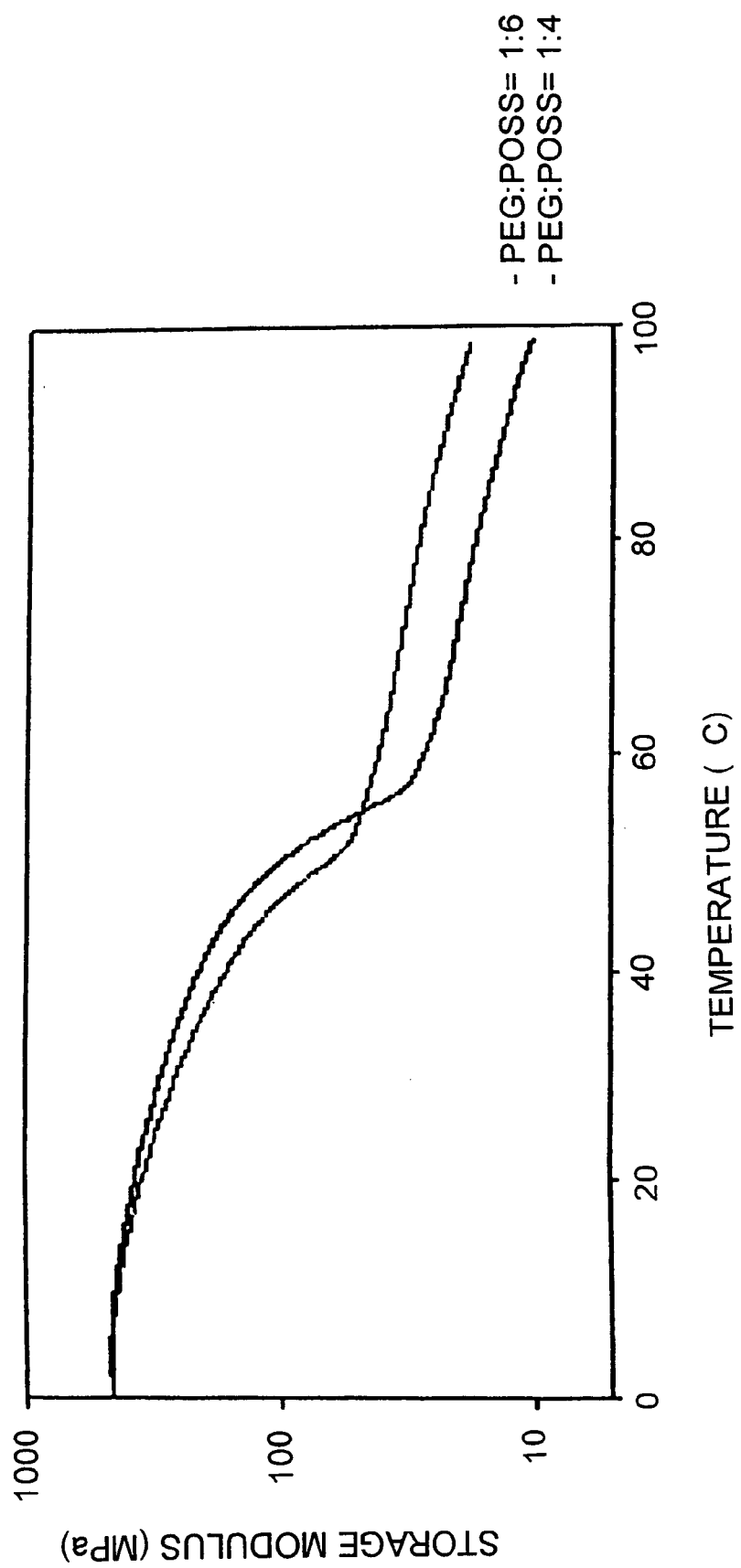
FIG. 8B is a graph of storage modulus as a function of temperature for several POSS polyurethanes.

The particular polyurethanes described directly above may be prepared the non-limiting schemes illustrated below. A graph of heat flow as a function of temperature for several POSS polyurethanes is shown in FIG. 8A and a graph of storage modulus as a function of temperature for several POSS polyurethanes is shown in FIG. 8B.

Scheme 1.

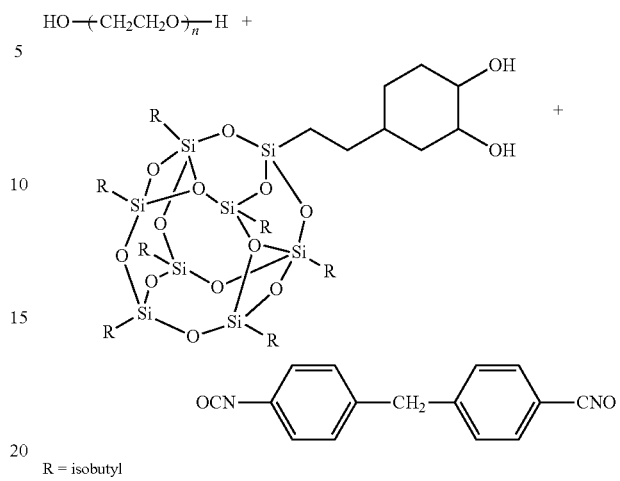

This scheme shows an example of synthesis of TPU using polyethylene glycol as polyol, TMP Isobutyldiol-POSS as chain extender to react with 4,4' diphenyl methylene diisocyanate in toluene.

Scheme 2.

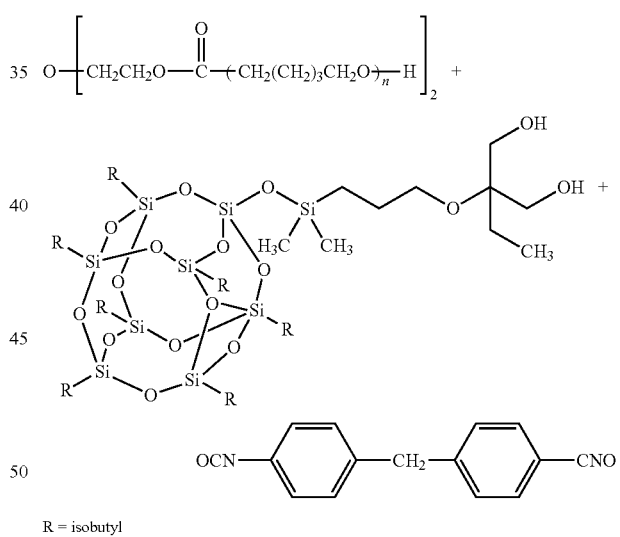

This scheme shows an example of synthesis of TPU using polycaprolactone diol as polyol, TMP Isobutyldiol-POSS as chain extender to react with 4,4' diphenyl methylene diisocyanate.

Scheme 3.

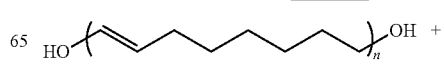

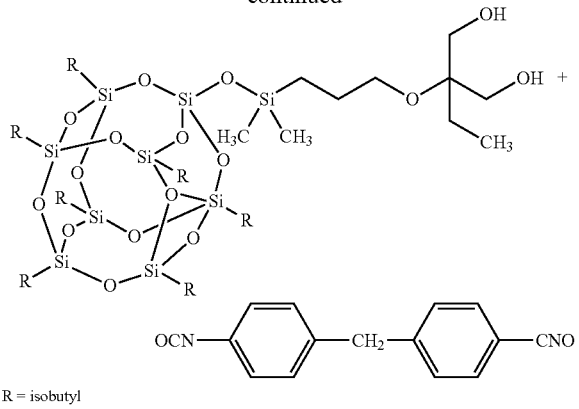

R = isobutyl

This scheme shows an example of synthesis of TPU using polyocyclooctene as polyol, TMP Isobutyldiol-POSS as chain extender to react with 4,4' diphenyl methylene diisocyanate.

Any of the polymers mentioned above may be filled with, for example, nanoparticles of clay and silica to, for example, increase the modulus of the plastic. Dispersing agents and/or compatibilizing agents may be used, for example, to improve the blending of polymers and the blending of polymers with fillers. Dispersing agents and/or compatibilizing agents include, for example, ACRAWAX® (ethylene bis-stearamide), polyurethanes and ELVALOY® (acrylic-functionalized polyethylene). The polymers can be cross-linked by application of radiation such as e-beam, UV, gamma, x-ray radiation or by heat-activated chemical crosslinking techniques. Radiation techniques provide the advantage that the polymer typically does not have to be substantially heated to achieve crosslinking. For e-beam radiation, an exposure of about 200-300, e.g. 250 kilograys, typically provides sufficient crosslinking.

Figure 9:
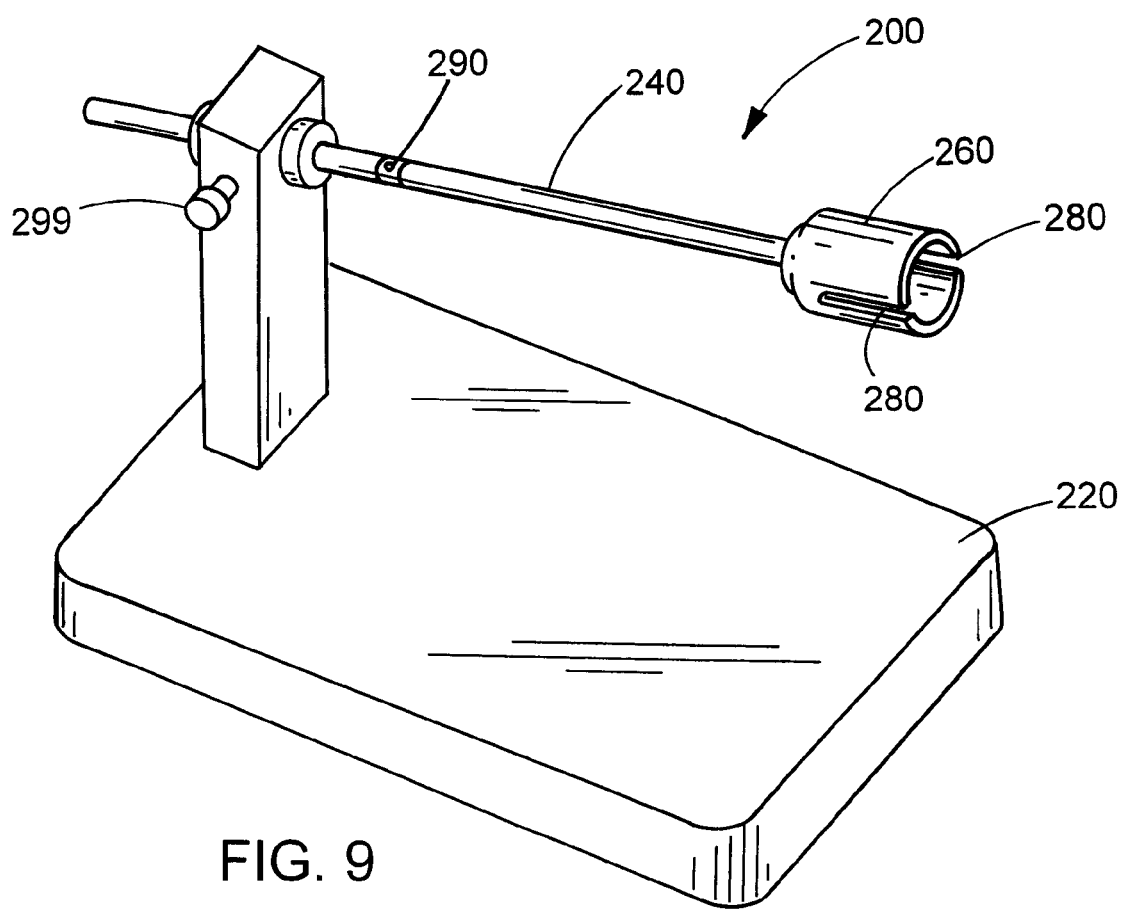
FIG. 9 is a perspective view of a wrapping fixture.

Referring to FIG. 9, wrapping fixture 200 can be used for making coiled stent 100. Wrapping fixture 200 includes a base 220 for support, a mandrel 240 with a flared end 260, slits 280 for fixing the plastic rod 120, an aperture 290 for fixing the plastic rod 120 on the non-flared end and a fixing screw 299 for releasably fixing mandrel 240 to wrapping fixture 200.

Stent 100 is manufactured from plastic rod 120 made by a variety of methods known in the art (e.g., extrusion, coextrusion, injection molding, casting, compression molding). If casting is used, the polymers may have tunable critical temperatures and rubber modulus have been synthesized using a thermosetting random copolymer formed from two vinyl monomers that yield controlled $T_g$ and casting-type processing. Such copolymers were crosslinked with a difunctional vinyl monomer (crosslinker), the concentration of crosslinker controlling the rubber modulus and thus the work potential during recovery. Rod 120 may have a diameter, for example, of about 0.25 mm to about 2.5 mm or more. Plastic rod 120 and wrapping fixture 200 are heated to the softening temperature of the polymer, making the plastic rod 120 malleable. The rod 120 is inserted into aperture 290 that is machined through mandrel 240 to fix the rod at the starting end. The rod 120 is tightly wrapped around mandrel 240, including flared end 260. To fix plastic rod 120 in place, plastic rod 120 is pushed into slits 280. The overall length of the stent 100 may be, for example, about 2 mm to about 150 mm or more. The overall length required depends upon the application. The plastic rod 120, now fixed in place on the mandrel 240, is heated to above the softening point of the material and maintained at that temperature long enough to anneal the rod and fix the shape. Typically, the time required to fix the shape is from about 0.25 hr to 10 hr or more. After cooling, stent 100 is removed from mandrel 240. Before packaging, the flared end of the coil is tapered down and collapsed so that the diameter along the entire length of the stent is approximately $d_1$. Collapsing the flared end 160 of stent 100 allows for ease of insertion, for example, into a restricted prostatic urethra.

EXAMPLE 1

A 56:24:20 mixture of PVAc/PVDF/PMMA is dry bended and loaded into the hopper of an extruder. The PVAc is grade B-100, the PVDF is Solvay SOLEF® 1010 and the PMMA is Atofina PLEXIGLAS® V045. The mixture is melt processed to produce 1.27 mm (0.05 inch) monofilament. The rod is made into a coil by winding it around wrapping fixture 200. The fixture and the rod are immersed into a 50° C. water bath. At this temperature, the rod becomes malleable enough to wind easily around the mandrel and secured in place to prohibit the uncoiling of the helical shape. The mandrel is removed from the fixture with the stent locked in place and placed into an oven at 110° C. for one hour to anneal the stent. This annealing process locks the permanent shape of the coil. The mandrel and coil are cooled to room temperature, and the stent is removed from the mandrel. The stent had on overall length of approximately 73 mm and a flared end portion length of approximately 7 mm. The diameter $d_1$ of the body is approximately 6 mm and the maximum diameter $d_2$ of the flare on the open end is approximately 11 mm. Before packaging, the flared end of the coil is tapered down with brief heating to 50° C. and manipulation, followed by cooling, so that the diameter is approximately 6 mm along the entire length of the stent.

Example 2

A 70:30 mixture of PVAc/PVDF is dry bended and loaded into the hopper of an extruder.

The mixture is melt processed to produce 1.27 mm (0.05 inch) monofilament. The rod is made into a coil by winding it around wrapping fixture 200. The fixture and the rod are immersed into a 50° C. water bath. At this temperature, the rod becomes malleable enough to wind easily around the mandrel and secured in place to prohibit the uncoiling of the helical shape. The mandrel is removed from the fixture with the stent locked in place and placed into an oven at 110° C. for one hour to anneal the stent. This annealing process locks the permanent shape of the coil. The mandrel and coil are cooled to room temperature, and the stent is removed from the mandrel. The stent had on overall length of approximately 73 mm and a flared end portion length of approximately 7 mm. The diameter $d_1$ of the body is approximately 6 mm and the maximum diameter $d_2$ of the flare on the open end is approximately 11 mm. Before packaging, the flared end of the coil is tapered down with brief heating to 50° C. and manipulation, followed by cooling, so that the diameter is approximately 6 mm along the entire length of the stent.

Figure 10:
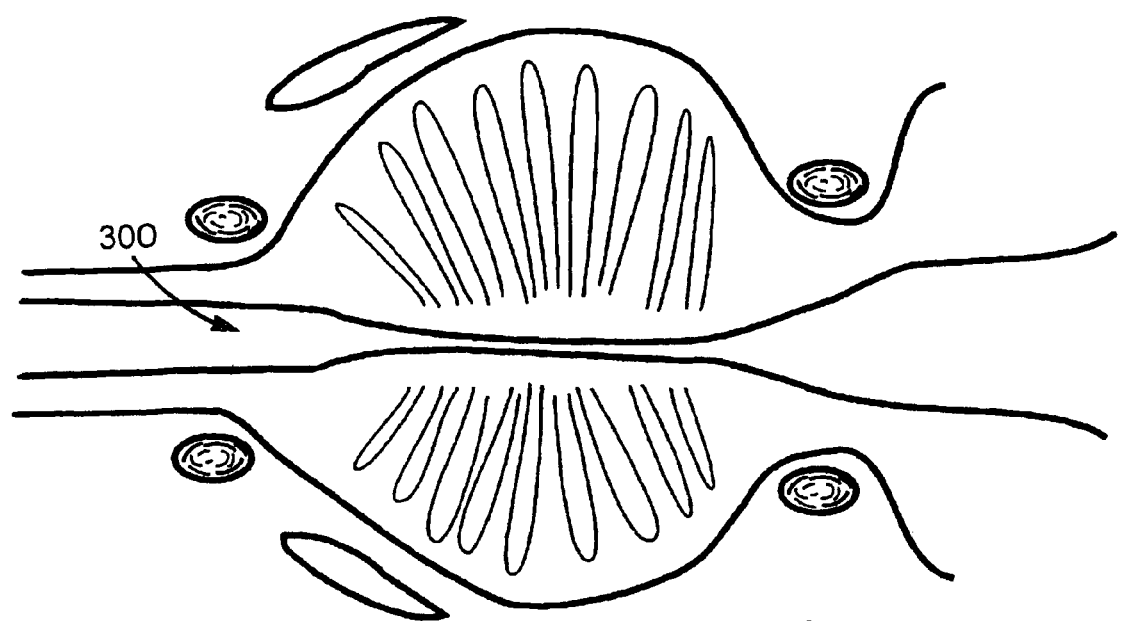
FIG. 10 is a cross-sectional view of a restricted prostatic urethra.

Referring to FIG. 10-12, stent 100 may be, for example, inserted into restricted urethra 300 on delivery tube 320. During insertion, end portion 160 is in a collapsed position. After insertion, warm water (e.g., 45° C.-55° C.) is flushed through delivery tube 320 that is in thermal contact with stent 100. Heating reverts the collapsed end 160 to a flared, expanded position (FIG. 12). The flared, expanded position allows stent 100 to remain fixed in position, for example, in the prostatic urethra.

Figure 13:
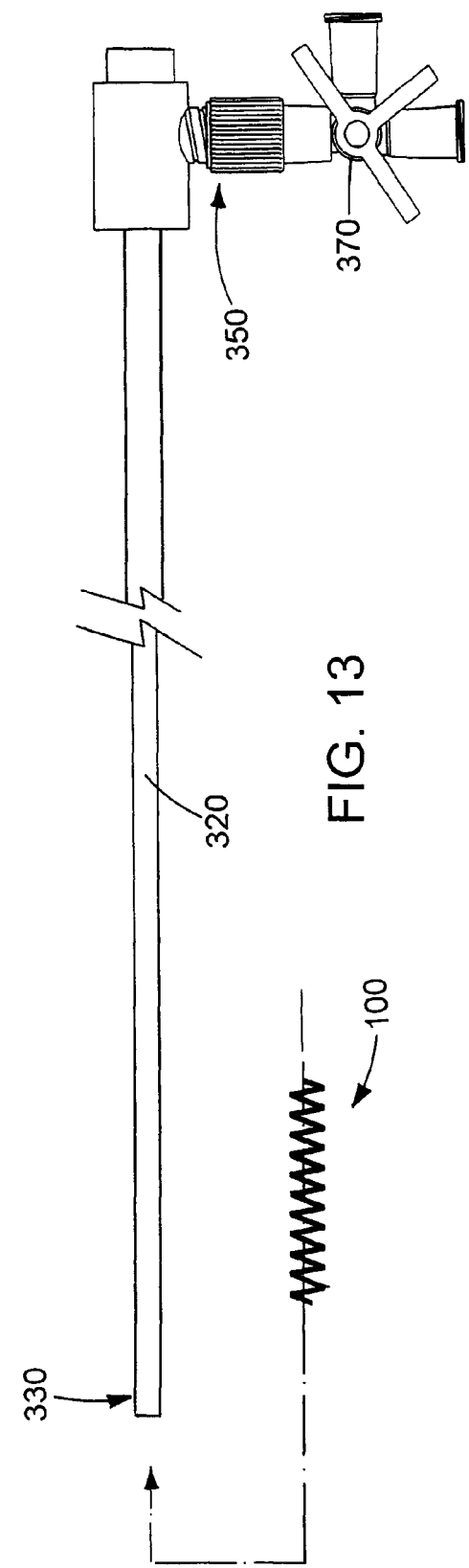
FIG. 13 is a side view of an alternative delivery system.

Referring to FIG. 13 for a little more detail, delivery tube 320 is a long cylindrical tube into which a ureteral scope 380 is inserted. Delivery tube 320 has a distal end 330 over which stent 100 is placed. Delivery 320 is fitted with a side port 350 including a stopcock 370 through which saline can be flushed for irrigation. Delivery tube 320 with stent 100 in place is delivered into, for example, the prostatic urethra with the aid of a ureteral scope. Once stent 100 is in place, hot saline is flushed through port 350 to revert the collapsed end 160 to a flared, expanded position (FIG. 12). The flared, expanded end allows stent 100 to remain fixed in position, for example, in or adjacent the prostatic urethra or external sphincter between the prostate and the bladder to prevent migration. The direction of the flare can, of course, be oriented in other directions. The scope and delivery tube 320 are withdrawn, leaving stent 100 in place.

Referring to FIGS. 13-13B, an alternative delivery system is illustrated that includes a tube 320 with a screw on tip 331 onto which a stent 100 is placed after collapsing the end portion 160. The assembly is inserted into, for example, the prostatic urethra.

Other delivery methods are within the claims. Stent 100 may be, for example, inserted into restricted urethra 300 on balloon catheter (not shown). During insertion, end portion 160 is in a collapsed position. After insertion, warm water is flushed through the guide wire lumen of the balloon catheter to flood the area and to heat the stent. Heating of the stent by the water reverts the collapsed end 160 to a flared, expanded position The flared, expanded position allows stent 100 to remain fixed in position, for example, in the prostatic urethra. If there is an obstruction in the lumen into which the stent is deployed the stricture can be dilated using the balloon to help the stent open fully and maintain a uniform diameter inside the vessel.

Figure 14:
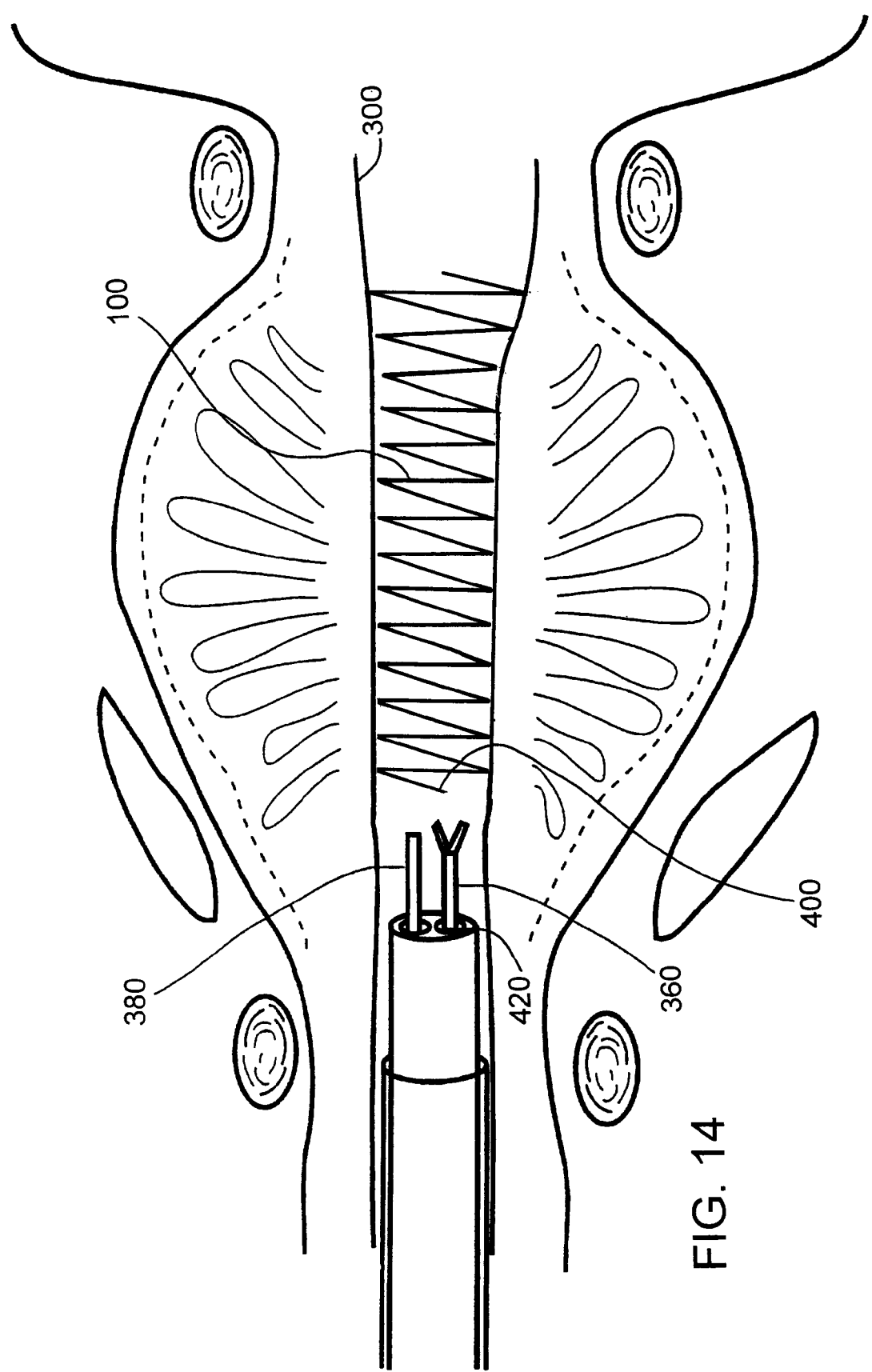
FIG. 14 is a cross-sectional view illustrating removal of a prostatic stent.

Referring to FIG. 14, coiled stent 100 with an end 160 in the expanded position can be removed with the aid of a catheter equipped with a grasping device 360 and a ureteral scope 380 for visualizing stent 100 in, for example, the prostatic urethra. Once end 400 of stent 100 has been visualized with ureteral scope 380, the stent is grasped with grasping device 360. Next, ureteral scope 380 is removed from the catheter and is replaced with a heating device (not shown), e.g. a catheter. Heating stent 100 above the softening point of the polymer, e.g., from about 45° C. to about 55° C. for polycyclooctene (PCO), and pulling the end 400 of stent 100 through the orifice 420 allows the stent to be removed in a substantially uncoiled state.

Although FIG. 11 shows heating of stent 100 with a warm liquid on a delivery tube, other heating methods are possible. For example, heating may be accomplished with the use of IR, RF or inductive heating.

Although insertion into a prostatic urethra has been used as an example, insertion of stent 10 into other body lumens or cavities is possible. For example, other body lumens or cavities include the biliary duct, cystic duct, a ureter, a bulbar urethra or a hepatic duct.

Figure 15:
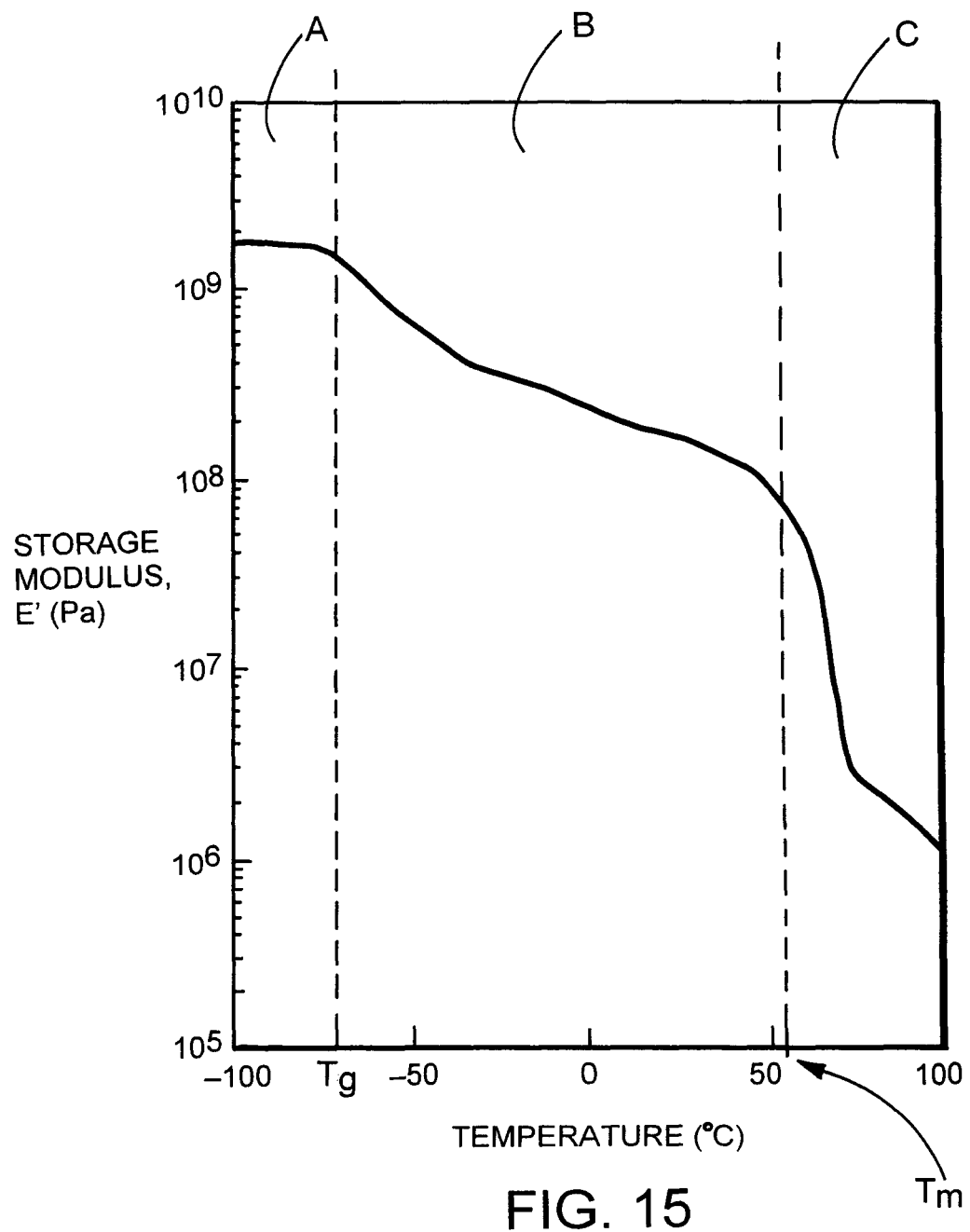
FIG. 15 is a graph of storage modulus (E') VS temperature for PCO.

Referring to FIG. 15, the modulus of polycyclooctene (PCO) that can, for example, be the polymer of stent 100 is shown as a function of temperature. Below approximately −65° C. ($T_g$, region A), PCO exists a rigid, glassy polymer. Above $T_g$, but below $T_m$, PCO exists as a flexible elastomer (region B). Above $T_m$, PCO exists as a relatively low modulus elastomer. Above $T_m$, for example, stent 100 composed of PCO can be removed from a lumen or cavity of the body, the prostatic urethra, for example, in a substantially uncoiled state.

Figure 16:
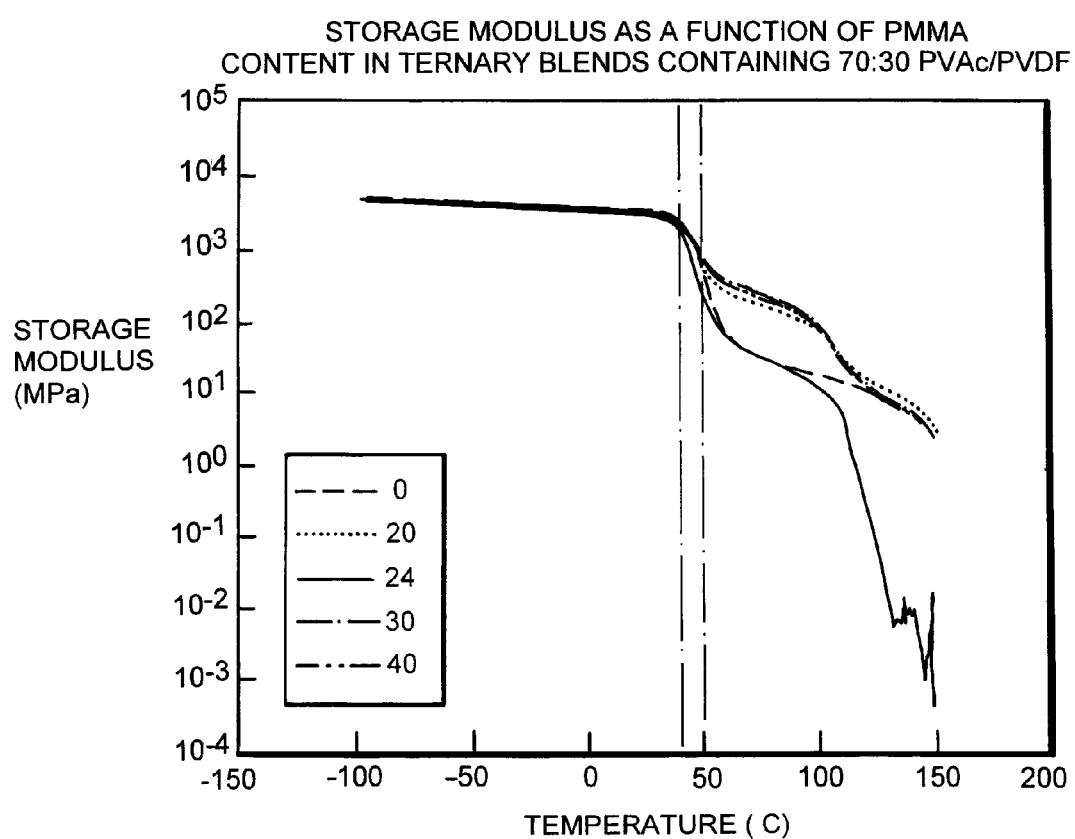
FIG. 16 is a graph of storage modulus (E') VS temperature for PVAc/PVDF/PMMA blends.

Referring to FIG. 16, the modulus of a ternary blend of PVAc/PVDF/PMMA that can, for example, be the polymer of stent 100 is shown as a function of temperature. Adding PMMA offers the advantage, for example, of increasing the modulus of the blend.

Referring once again to FIG. 15 and to FIGS. 6-8, heating stent 100 in the expanded position briefly above $T_m$ (region C) and then cooling rapidly below $T_m$ (e.g., region B) "freezes" stress into stent 100. Stent 100 reverts from its collapsed position to its expanded position upon re-heating above $T_m$ (region C) because the modulus of the material lowers sufficiently to release the residual stress that was "frozen" into stent 100 during the rapid cooling.

FIGS. 17-28 show other examples of stents.

Figure 17:
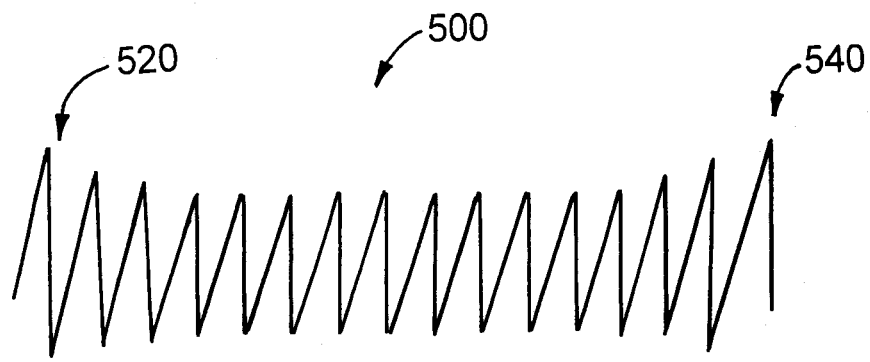
FIG. 17 is a side view of an alternative stent with two ends portions in expanded positions.
Figure 18:
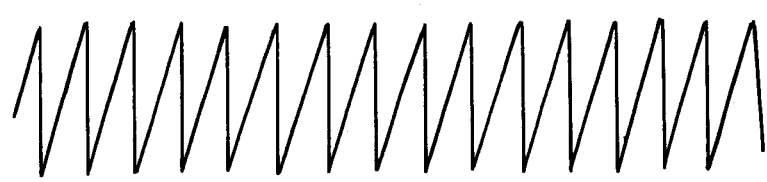
FIG. 18 is the stent shown in FIG. 17 with ends in collapsed positions.

Referring to FIGS. 17 and 18, coiled stent 500 has two end portions 520 and 540 in expanded positions. End portions 520 and 540 can be collapsed (FIG. 18) for ease of insertion into a body cavity or lumen, and reverted with heat to expanded positions.

Figure 19:
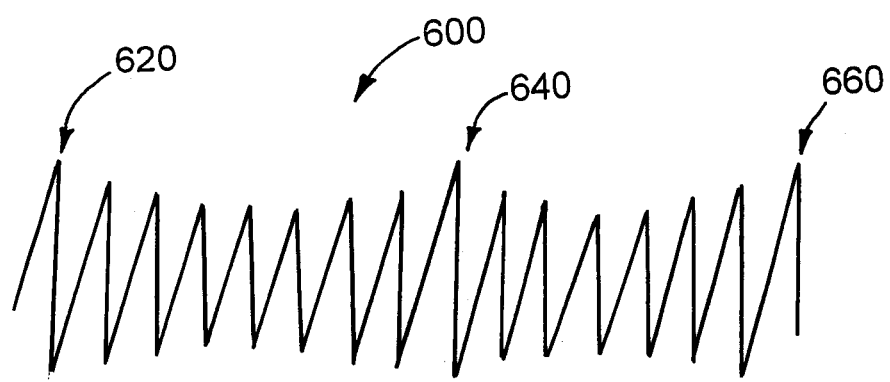
FIG. 19 is a side view of an alternative stent with three portions in expanded positions.

Referring to FIG. 19, coiled stent 600 has two end portions 620 and 660 and a central portion 640 in expanded positions. All three portions may be collapsed (not shown), and then reverted to expanded positions.

Figure 20:
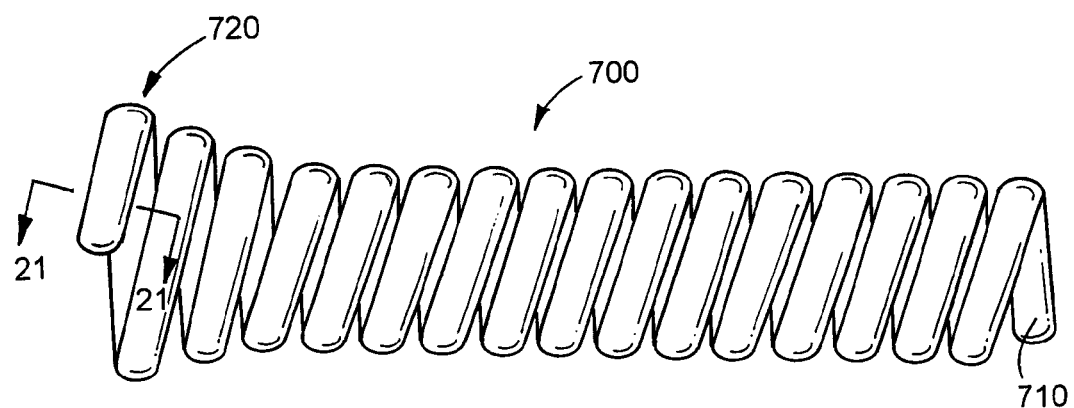
FIG. 20 is a side view of an alternative stent made with a flattened tube.
Figure 21:
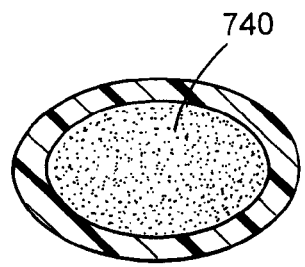
FIG. 21 is a cross-sectional view of the stent shown in FIG. 20, taken along 21-21.

Referring to FIGS. 20 and 21, coiled stent 700 made from a flattened tube 710 has an end portion 720 in an expanded position. The flattened tube can, for example, add strength to the stent. The tube can have a major diameter, for example, of between about 1.0 mm to about 3.0 mm, more preferably between about 1.5 mm to about 2.25 mm, and major inner diameter, for example, of between about 0.5 mm to about 2.5 mm, more preferably between about 1.25 mm and about 1.75 mm. End portion 720 may be collapsed (not shown) and then reverted to an expanded position. Referring to FIG. 21, flattened tube 710 has an interior 740 that may be filled with, for example, a medicament. The medicament, for example, may be triclosan or salicylic acid. Release of medicament from flattened tube 710, for example, may reduce the risk of infection. Interior 740 may also be filled with, for example, paclitaxel or mitoxantrone. Release of the these medicaments from interior 740 may be, for example, useful for treating prostate cancer and reducing prostatic hyperplasia.

In general, any filler, e.g., a therapeutic agent, can be used to fill interior 740. A therapeutic agent can be a genetic therapeutic agent, a non-genetic therapeutic agent, or cells. Therapeutic agents can be used singlularly, or in combination. Therapeutic agents can be, for example, nonionic, or they may be anionic and/or cationic in nature.

Exemplary non-genetic therapeutic agents include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, and (r) hormones.

Exemplary genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Figure 22:
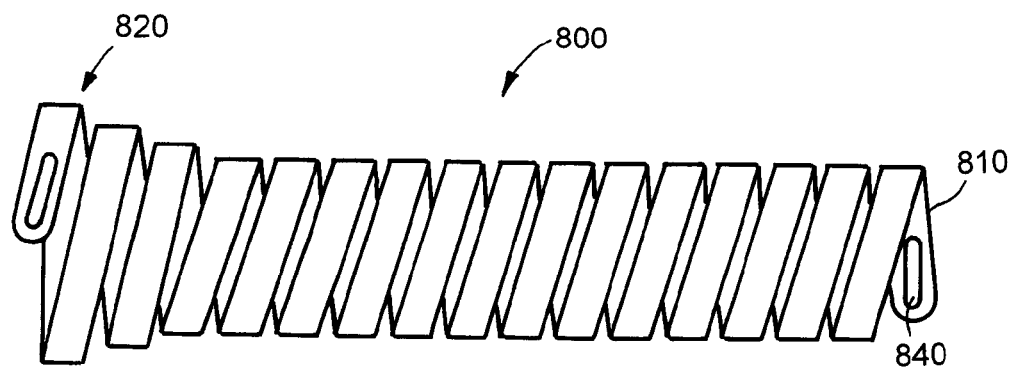
FIG. 22 is a side view of an alternative stent made with a tape.

Referring to FIG. 22, coiled stent 800 made from tape 810 has an end portion 820 that may be collapsed and then reverted to an expanded position. Tape 810, for example, may have a thickness from about 0.5 mm to about 2.0 mm, more preferably from about 0.75 mm to about 1.25 mm, and a width, for example, of from bout 1.0 mm to about 3.0 mm, more preferably from about 1.75 mm to about 3.00 mm. In this particular embodiment, an aperture 840 is provided so that a trailing string (not shown) can be included for ease of removal with the grasping device shown in FIG. 14.

Figure 23:
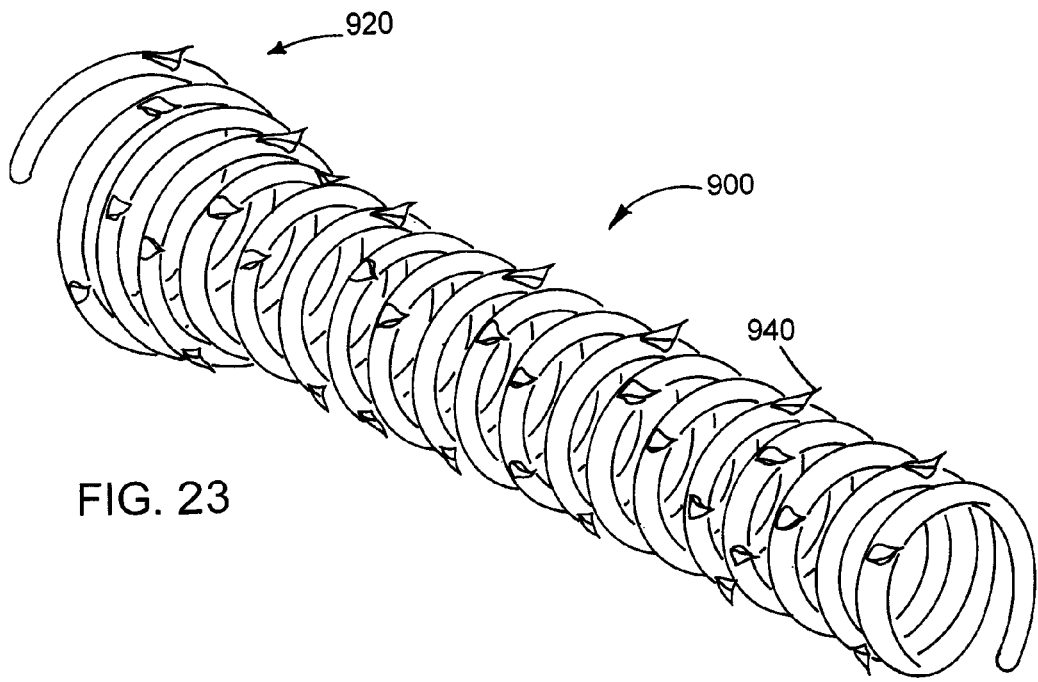
FIG. 23 is a perspective view of a stent with a plurality of protruding elements, the end of the stent is in an expanded position.
Figure 24:
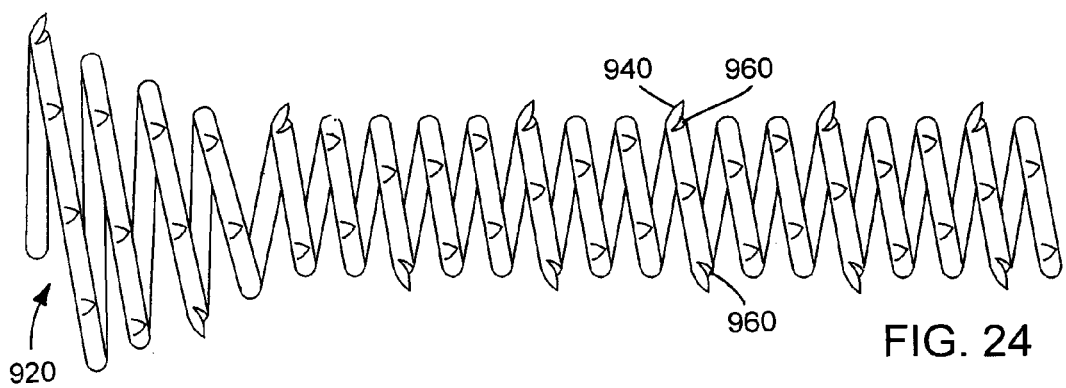
FIG. 24 is a side view of the stent shown in FIG. 23.
Figure 25:
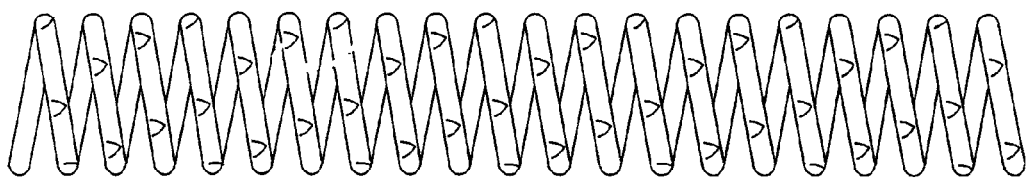
FIG. 25 is a side view of the stent shown in FIG. 23 with the end in a collapsed position.
Figure 26:
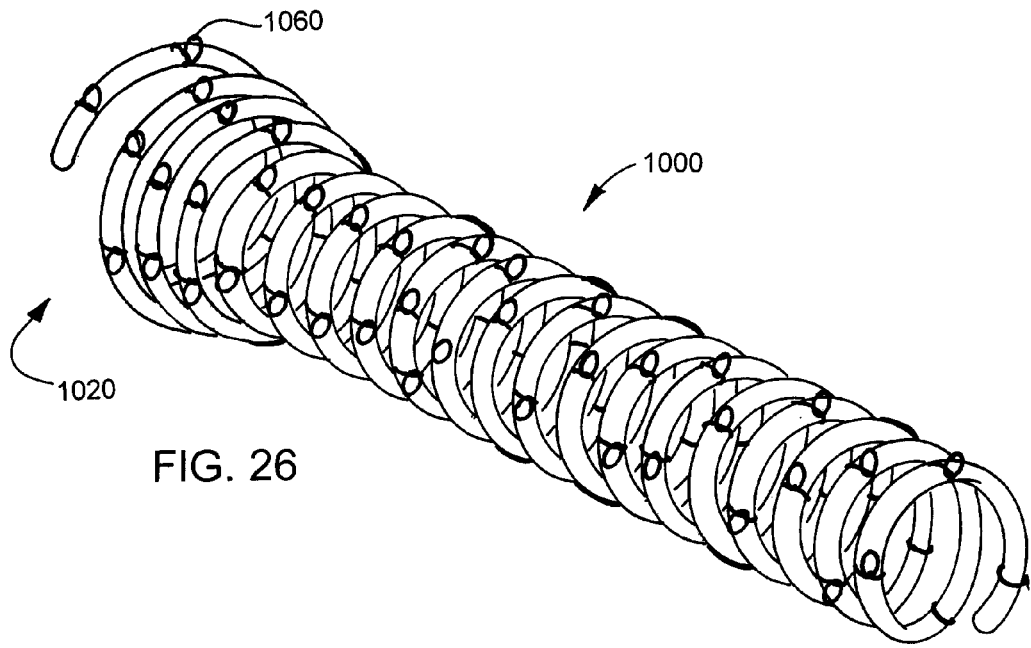
FIG. 26 is a perspective view of an alternative stent with a plurality of protruding elements, the end of the stent in an expanded position.
Figure 27:
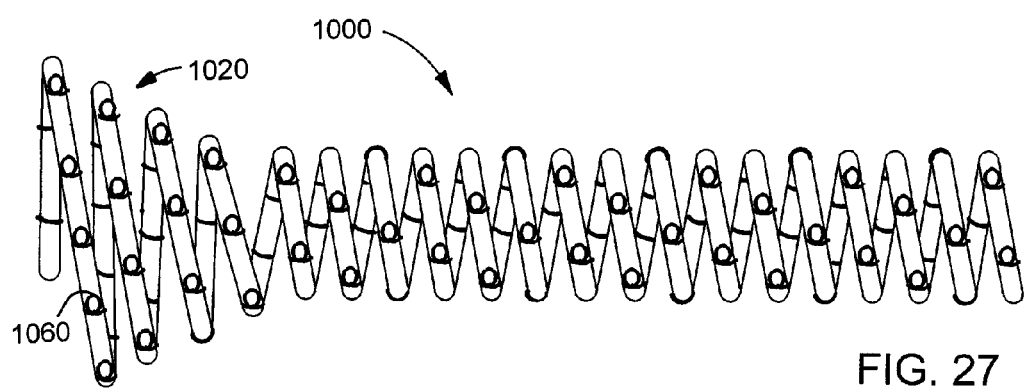
FIG. 27 is a side view of the stent shown in FIG. 26.
Figure 28:
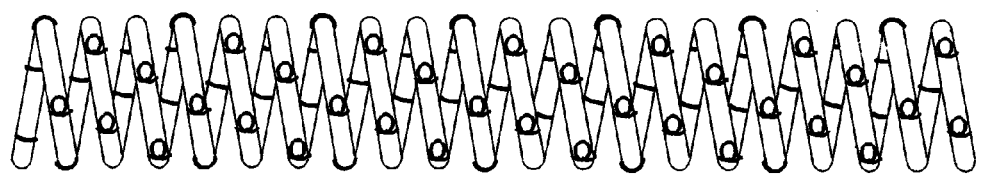
FIG. 28 is a side view of the stent shown in FIG. 26 with an end in a collapsed position.

Referring to FIGS. 23-25, coiled stent 900 is made from plastic rod and has an end portion 920 that may be collapsed and then reverted to an expanded position. Stent 900 includes a plurality of protruding elements 940 that are integral with and extend outwardly from the plastic rod from which the stent is made. Referring now to FIGS. 26-28, coiled stent 1000 is made from plastic rod, for example, oriented monofilament, and has an end portion 1020 that may be collapsed and then reverted to an expanded position. Stent 1000 includes a plurality of protruding elements 1060 that extend outwardly from the plastic rod from which the stent is made. The friction provided by protruding elements 940, 1060 can help to hold stent 900,1000 in place within, for example, the prostatic urethra.

Protruding elements 940 are made, for example, by cutting into the plastic rod with, for example, a sharp edged instrument, for example, a knife, so as penetrate a depth into the plastic rod. The depth of penetration P is adjusted to provide acceptable frictional properties, while minimizing the impact on the mechanical properties of the plastic rod. In some implementations, the maximum depth of penetration into the plastic rod, measured inwardly from the outer surface of the plastic rod is, for example, from about 1 to about 50% of the average thickness of the plastic rod. If the depth penetration is too large, the mechanical properties of the plastic rod may be reduced and if the depth of penetration is too low, the resulting protruding elements may be too small to provide the appropriate frictional properties when expanded in a body cavity or lumen, for example, the prostatic urethra. Other cutting means are possible, for example, water knife and laser cutting means, to reduce the impact of the cutting on the mechanical properties of the plastic rod. The shape of the plastic rod from which the stent is made may be of other forms than that shown above. For example, it may be in the form of, for example, a coiled elongated flattened tube and the flattened tube may include a central opening that includes a medicament that can be released by the inserted stent.

In some implementations, stent 900 is manufactured from plastic rod made by a variety of methods known in the art (e.g., extrusion and coextrusion). The plastic rod may have a diameter, for example, of about 0.25 mm to about 2.5 mm or more. In a preferred method, the protruding elements are put onto the plastic rod before wrapping the mandrel shown and discussed above. After wrapping the mandrel, the plastic rod and wrapping fixture 200 are heated to the softening temperature of the polymer, making the plastic rod malleable. The protrusions are annealed in the "up" position, that is, with the protruding elements extending outwardly by "prying up" the protruding elements that results from cutting. Prying up the protruding elements may be achieved by, for example, running a surface across the protruding elements in a direction opposite the cut direction. Annealing is continued to fix the shape. After cooling, the stent is removed from mandrel. Before packaging, the flared end of the coil is tapered down along with protruding elements and collapsed so that the diameter along the entire length of the stent is approximately $d_1$. Collapsing the flared end and protruding elements allows for ease of insertion, for example, into a restricted prostatic urethra. In some implementations, the flared end and the main body are collapsed to have a diameter less than $d_1$. Upon heating, the end portion reverts to its expanded position and the protruding elements revert to their up positions. If a medicament is placed in the cavities 960 from which the protruding elements 940 are carved, it may be released upon expansion of the stent.

Referring to FIGS. 26-28, stent 1000 with protruding elements 1060 is made by, for example, wrapping a thicker plastic rod with a thinner plastic rod, for example, a monofilament, that includes a plurality of constrictions, for example, knots along its length. The elevation E above an outer surface of the thicker plastic rod is adjusted to provide acceptable frictional properties. In some implementations, the maximum elevation above an outer surface of the thicker plastic rod is, for example, from about 1 to about 50% of the average thickness of thicker plastic rod. If the elevation E is too large, insertion of stent 1000 into, for example, a prostatic urethra may become difficult and if the maximum elevation above the protruding elements is too small, the protruding elements may not provide the appropriate frictional properties when expanded in a body cavity or lumen, for example, the prostatic urethra. The shape of the rods from which the stent is made may be of other forms than that shown above. For example, it may be in the form of, for example, a coiled elongated flattened tube and the flattened tube may include a central opening that includes a medicament that can be released by the inserted stent.

In some implementations, stent 1000 is manufactured from plastic rod made by a variety of methods known in the art (e.g., extrusion and coextrusion). The thicker plastic rod may have a diameter, for example, of about 0.25 mm to about 2.5 mm or more. The thinner plastic rod from which the protruding elements are fashioned may have a diameter of, for example, from about 0.2 mm to about 20 mm. In a preferred method, the constrictions, for example, knots, are placed on the thinner plastic rod and the thinner plastic rod is wrapped around the outer surface of the thicker plastic rod. The ends of the thinner plastic rod are heat staked to hold the thinner plastic rod onto the outer surface of the thicker plastic rod. Now, the assembly of the thinner and thicker plastic rod is wrapped around the mandrel shown and discussed above. After wrapping the mandrel, the plastic rods and wrapping fixture 200 are heated to the softening temperature of the polymer of the thicker plastic rod, making the plastic rod malleable Annealing is continued to fix the shape. After cooling, the stent is removed from mandrel. Before packaging, the flared end of the coil is tapered down so that the diameter along the entire length of the stent is approximately $d_1$. Collapsing the flared end and protruding elements allows for ease of insertion, for example, into a restricted prostatic urethra. In some implementations, the thinner plastic rod may contain a medicament that is released upon expansion, for example, in the prostatic urethra. In other implementations, the thinner plastic rod is made of a degradable material and the degradable material is filled with a medicament.

In some embodiments, the entire stent, for example, the stents of FIGS. 4, 5, 20, 23 and 26, may have an expanded position.

Referring to FIGS. 29 and 30, an implantable stent includes a tubular member 1102 that is formed from a polymeric material, e.g., PCO. Tubular member 1102 includes a wall with thickness $W_1$ and has a first transverse dimension $OD_1$, and a first longitudinal length $L_1$ that is measured at first transverse dimension. Tubular member 1102 is sized for delivery into a lumen. Upon exposure to an elevated temperature, e.g., 40, 50, or 60° C., and to outward mechanical forces, e.g., delivered by a balloon, tubular member 1102 can be expanded (FIG. 30) to a second transverse dimension $OD_2$ that is, e.g., about fifty percent larger than the first transverse dimension $OD_1$ within the lumen. First and second transverse dimensions are measured from an outer surface 1106, 1108 of the tubular structure in its unexpanded and expanded state, respectively. In its expanded state, the tubular member has a wall with thickness $W_2$ and a second longitudinal length $L_2$, measured when at the second transverse dimension. After expansion from the first $OD_1$ to the second $OD_2$ transverse dimension, the second longitudinal length $L_2$ decreases by less than about fifty percent, measured relative to the first longitudinal length $L_1$. This reduced forshortening can improve, for example, placement accuracy within the lumen.

FIGS. 31 and 32 show an embodiment employing an elongated tubular member 1110 that can be expanded in a manner similar to that described above in reference to FIGS. 29 and 30. FIGS. 31 and 32 illustrate that stents having reduced foreshortening can be configured to have a variety of dimensions to enable the stents to be used in a variety of lumens within the body. Referring particularly to FIG. 31, the unexpanded tubular structure has an unexpanded transverse dimension $OD'_1$, an unexpanded length $L'_1$ and an unexpanded wall thickness $W'_1$. Referring particularly to FIG. 32, the expanded tubular member has an expanded transverse dimension $OD'_2$, an expanded length $L'_2$ and an expanded wall thickness $W'_2$.

In some embodiments, the wall thickness of the tubular member decreases by greater than about twenty percent, e.g., greater than about fifty percent, greater than about fifty-five percent, greater than about sixty percent, greater than about sixty-five percent, greater than about seventy-five percent, or more, e.g., greater than about ninety percent, after expansion from the first transverse dimension to the second transverse dimension. Without wishing to be bound by any particular theory, it is believed that a relatively large decrease in the wall thickness in going from the unexpanded state to the expanded state at least partially explains the observed reduced foreshortening.

In specific embodiments, after expansion from the first transverse dimension to the second transverse dimension that is at least about seventy-five percent larger than the first transverse dimension, the second longitudinal length decreases by less than about thirty percent, e.g., less than twenty-five percent, less than twenty percent, less than fifteen percent, or less than ten percent, measured relative to the first longitudinal length.

In a specific implementation, the tubular member is approximately circular in transverse cross-section. In other embodiments, the tubular member has other shapes in transverse cross-section. For example, the tubular member can be square, rectangular, pentagonal, hexagonal, octagonal, or elliptical in transverse cross-section.

Generally, the polymeric material has relatively low softening temperature so that high temperatures do not need to used within the body. For example, the polymer can have a softening temperature from about 40° C. to about 60° C., e.g., 45, 50, 55, or 58° C.

The polymeric material can be non-cross-linked, cross-linked, shape memory, or non-shape memory. Generally, suitable polymeric materials include those discussed above, e.g., nylons, polyurethanes, or PVAc/PVDF blends, and those discussed below. Specific polymeric materials include polycyclooctene (PCO), styrenic elastomers, styrenic block copolymers, styrene-butadiene rubber, polyolefins, trans-isoprene, plasticized PVC, e.g., PVC plasticized with a monomeric plasticizer, e.g., a phthalate, or a polymeric plasticizer, or blends of these polymers. In some embodiments, the polymeric material has an elastic modulus of greater than about 50,000 psi, e.g., greater than about 75,000, greater than about 100,000, greater than about 200,000, greater than about 250,000, or more, e.g., greater than about 500,000 psi. Without wishing to be bound by any particular theory, it is believed that proper selection of the polymeric material at least partially explains the observed reduced foreshortening.

The polymeric material can include fillers, e.g., a radio-opaque agent, or a thermal conductor. Examples of radio-opaque materials include bismuth carbonate, barium sulfate, or mixtures of these materials. Examples of thermal conductors include a boron nitride, a metal, or mixtures of these materials.

A stent can have a shape in memory, e.g., a curved shape. For example, the stent can have an unexpanded shape that is substantially straight, and an expanded shape that is curved (FIG. 33). A curved tubular member can enable better retention in a deployed region of the lumen such that the stent has a reduced likelihood for movement within a lumen. Other memorized shapes are possible. For example, the stent may have a flared end, or two flared ends after expansion, as shown in FIG. 34. Flared ends can also enable better retention in a deployed region of a lumen.

Referring now to FIGS. 32 and 35, a stent can have a smooth outer surface after expansion, like that of FIG. 32, or the stent can have an outer surface that includes a plurality of protruding elements 1112 after expansion, like that of FIG. 35. As was discussed in reference to FIG. 23, the friction provided by the protruding elements can help hold the stent in place within a lumen.

Referring back to FIG. 31, a tubular member can include apertures 1114 defined in a wall, when this is desired. In some embodiments, apertures are advantageous because they can allow tissue to grow into the apertures, thereby enabling better retention in the lumen.

In some embodiments, the tubular member is delivered to a lumen, e.g., a pulmonary lumen, an esophageal lumen, a biliary lumen, an enteral lumen, a ureteral lumen, or a urethral lumen. Delivery to the lumen can be done on, e.g., a balloon catheter. After expansion of the tubular member within the lumen, the delivery vehicle can be removed, with the stent remaining in place within the lumen of the patient.

In a specific embodiment, an unexpanded tubular stent is cylindrical in shape, has a smooth outer surface, and is made of PCO filled with about forty percent by weight of a boron nitride for radio-opacity, and for enhanced thermal conductivity. The stent has an unexpanded wall thickness of about 3 mm, an outer diameter of approximately 10 french, and an unexpanded length of approximately 25 mm. After expansion on a heated balloon at 50° C., followed by cooling to set the shape of the stent, an expanded wall thickness is approximately 1 mm, an outer diameter is approximately 20 french, and an expanded length is approximately 20 mm.

Other Embodiments

In some of the embodiments of any of the above stents, only a portion or portions of the stent (e.g., the portion(s) having an expanded position) may be composed of the polymer. The remainder of the stent may be, for example, composed of a non-polymeric material (e.g., a metal or metal alloy, e.g., Ni/Ti alloy). Moreover, the stent may be composed of multiple layers of materials, for example, by co-extruding the layers when making an elongated element. The stent may be a multiple segment stent.

The polymer in any of the above stents may be a blend of polymers, for example, miscible blends of a semicrystalline polymers with an amorphous polymer. For those blends that are miscible at the molecular level, a single glass transition results, without broadening. Additionally, in such miscible blends the equilibrium crystallinity (which controls the plateau modulus between $T_g$ and $T_m$ where shape fixing is performed) also changes dramatically and systematically with blend composition; i.e., relative levels of each component.

Polymers blends with a relatively high modulus in the fixed state at room temperature, having a tunable and sharp transition, the permanent shape of which can be remolded repeatedly above certain melting temperatures are prepared by the blending of crystalline polymers (C') with amorphous polymers (A'), such that they are a single miscible phase in the molten state (allowing processing to stress-free native states) but crystalline to a limited and tailored extent and which further vitrify on cooling to room temperature. The recovery of the polymer blend may be fast, for example, within seconds. Examples for (C') include poly(vinylidene fluoride) (PVDF) ($T_g$=−35° C., $T_m$=175° C.), polylactide (PLA) ($T_g$=56° C., $T_m$=165° C.), poly(hydroxy butyrate), poly(ethylene glycol) (PEG), polyethylene, polyethylene-co-vinyl acetate, poly(vinyl chloride) (PVC), and poly(vinylidene chloride) (PVDC) and copolymers of poly vinylidene chloride (PVDC)/poly vinyl chloride (PVC). Examples for (A') include poly(vinyl acetate) (PVAc) ($T_g$=35° C.), poly methyl acrylate (PMA), poly ethyl acrylate (PEA), atactic poly methyl methacrylate (aPMMA), isotactic poly methyl methacrylate (iPMMA), syndiotactic poly methyl methacrylate (sPMMA), and other poly alkyl methacrylates.

In some preferred embodiments formed from two miscible polymer blends, the blend is prepared by mixing amorphous poly(vinyl acetate) (PVAc) ($T_g$=35° C.) with semicrystalline polylactide (PLA) ($T_g$=56° C., $T_m$=165° C.) or poly(vinylidene fluoride) (PVDF). The polymers show complete miscibility at all blending ratios with a single glass transition temperature, while crystallization (exclusive of PVAc) is partially maintained. The $T_g$'s of the blends are employed as the critical temperature for triggering the shape recovery while the crystalline phases serve as physical crosslinking sites for elastic deformation above $T_g$, but below $T_m$.

The preferred blends are formed from poly vinyl acetate (PVAC) and poly(lactic acid) (PLA) or poly(vinylidene fluoride) (PVDF). However, examples of other suitable blends include the pair PVDF/PMMA and ternary blends of PVDF/PMMA/PVAc. The PMMA and the combination of PMMA/PVAc serve the same role as PVAc in the blends as have been previously described. An advantage of adding PMMA is that the critical temperature can be increased arbitrarily to about 80° C. and the room temperature modulus can also be increased. The PVDF may be substituted by poly(vinylidene chloride) (PVDC), by copolymers of poly(vinylidene chloride/ply(vinyl chloride), or by any "C" polymer vide supra.

It has further been found that blending poly(vinyl chloride) with poly(butyl acrylate) or poly(butyl methacrylate) (PVC/PBA) has certain advantages. In the PVDF/PVAc case, PVAc simultaneously lowers the crystallinity of PVDF while increasing $T_g$. PVC may serve the same role as PVDF, but it already has a low degree of crystallinity, but a relatively high $T_g$ (~80° C.). Thus in this embodiment, the second component (PBA) serves only the role of decreasing $T_g$. This can also be achieved with small molecule plasticizers, most notably dioctylphthalate (DOP), but is preferred to use a biocompatible polymeric plasticizer for intended implantable applications. The range of PBA compositions is 10-40%, with 20% being the most advantageous, yielding a $T_g$~40° C.

Melt blending of PLA/PVAc and PVDF/PVAc of varying blend ratios was performed in a 30 ml Brabender mixer. The mixer was equilibrated at T=180° C. for 5 minutes after which the mixer blade rotation was adjusted to 25 RPM and the premixed polymers pellets added to the chamber over the course of 1 minute. The polymers were mixed for 10 minute to ensure good dispersion. Nitrogen was purged through the chamber to mitigate potential oxidative degradation during mixing. After mixing, the blend was taken out of the chamber, cooled to room temperature, and then pressed between heated platens of a Carver press at 180° C. for 5 minutes under a load of 8 metric tons. A spacer was used to control the thickness of the film and rapid cooling to room temperature was carried out. The films thus formed were used for the subsequent thermal and mechanical characterization.

The TGA results demonstrated that both PLA and PVAc are stable for T<300° C. Above this temperature PLA degrades completely (no char yield), while the PVAc degrades to yield an intermediate char yield of 25 wt % for 375<T<425° C. but complete degradation above 450° C. Blend processing and thermal and dynamic mechanical analyses (DSC and DMA) were performed below 250° C., to completely avoid degradation.

Figure 36:
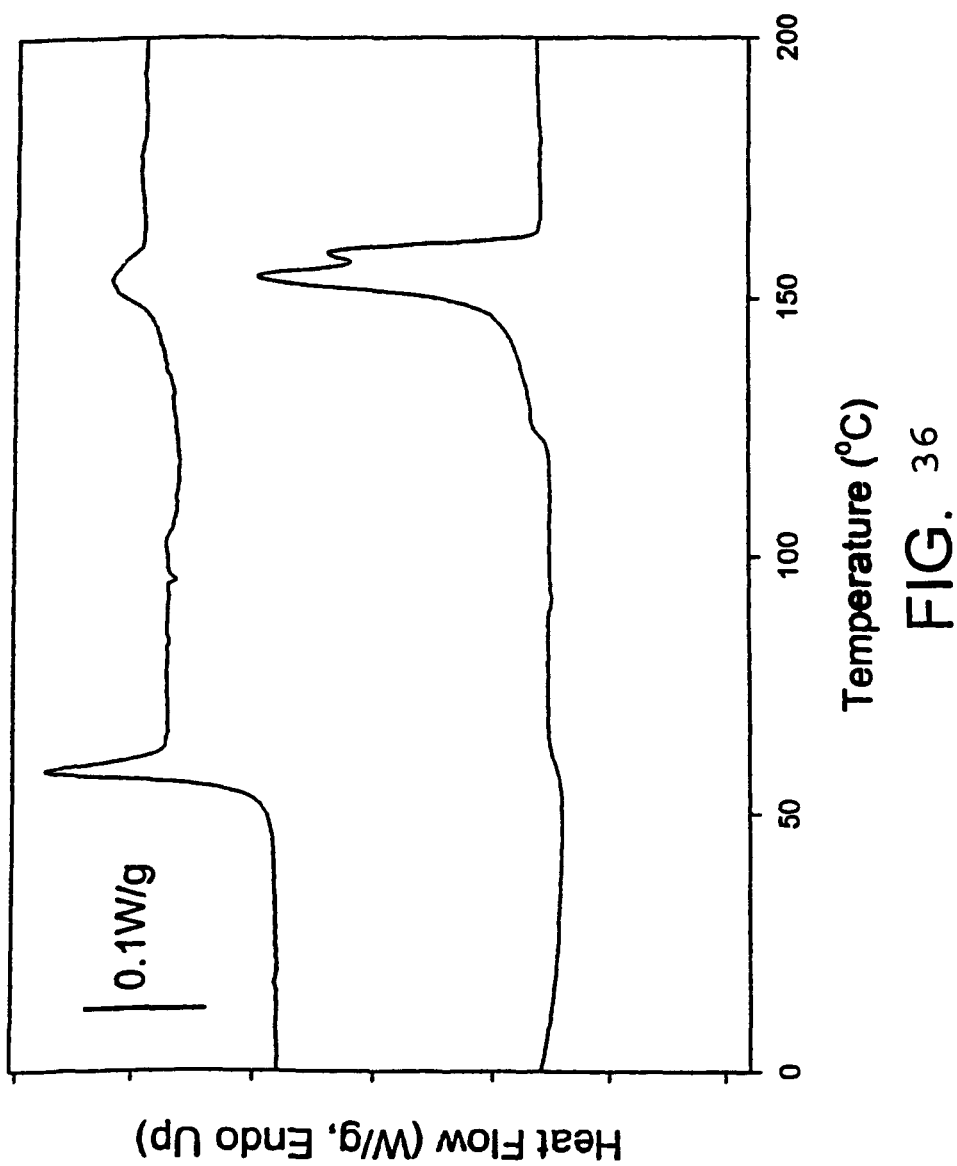
FIG. 36 shows DSC traces of PLA (top) quenched from T=180° C. or (bottom) annealed at T=110° C. for 1 hr.

The crystallization behavior of semicrystalline PLA was investigated via DSC. The PLA samples were first heat pressed at 180° C. for 10 minutes and then quenched to room temperature with water cooling. One sample was directly analyzed by DSC, while another was first annealed at 110° C. (=½($T_g$+$T_m$)) for 1 hour to reach an equilibrium level of crystallinity. FIG. 36 shows a comparison of thermal behavior for these two samples. It was observed that quenching the PLA melt results in a low degree of crystallinity and virtually no recrystallization on heating, both indicating slow crystallization Annealing at 110° C. for 1 hour results in significant crystallization evidenced by a large melting endotherm at T=155° C. The melting temperature did not shift dramatically due to annealing, but the endotherm shape did change. Complementary WAXD experiments yielded the same conclusions.

Figure 37:
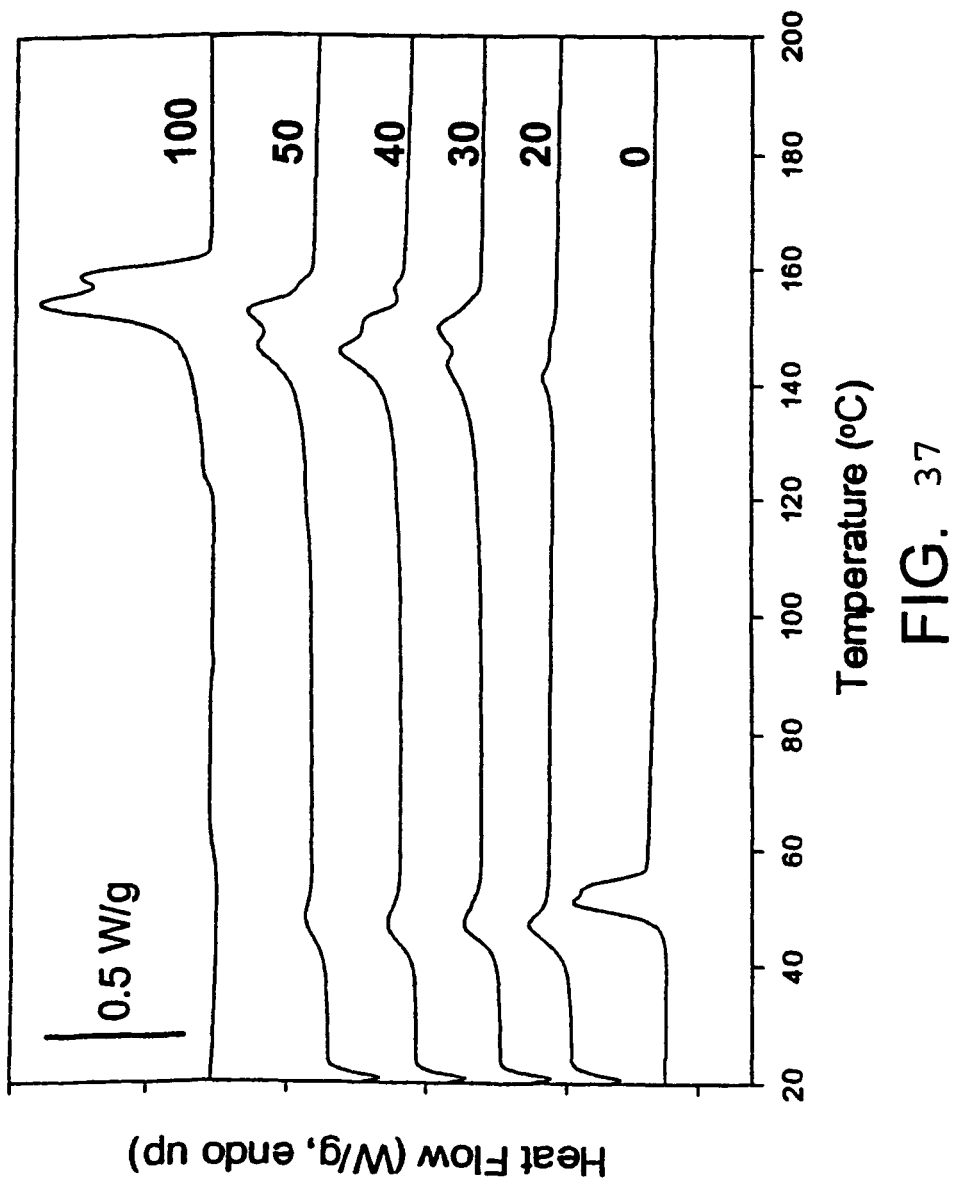
FIG. 37 shows DSC traces for PLA/PVAc blends following annealing for 1 hour at T=110° C. A heating rate of 10° C./min was employed. PLA weight percent is indicated with each trace.
Figure 38:
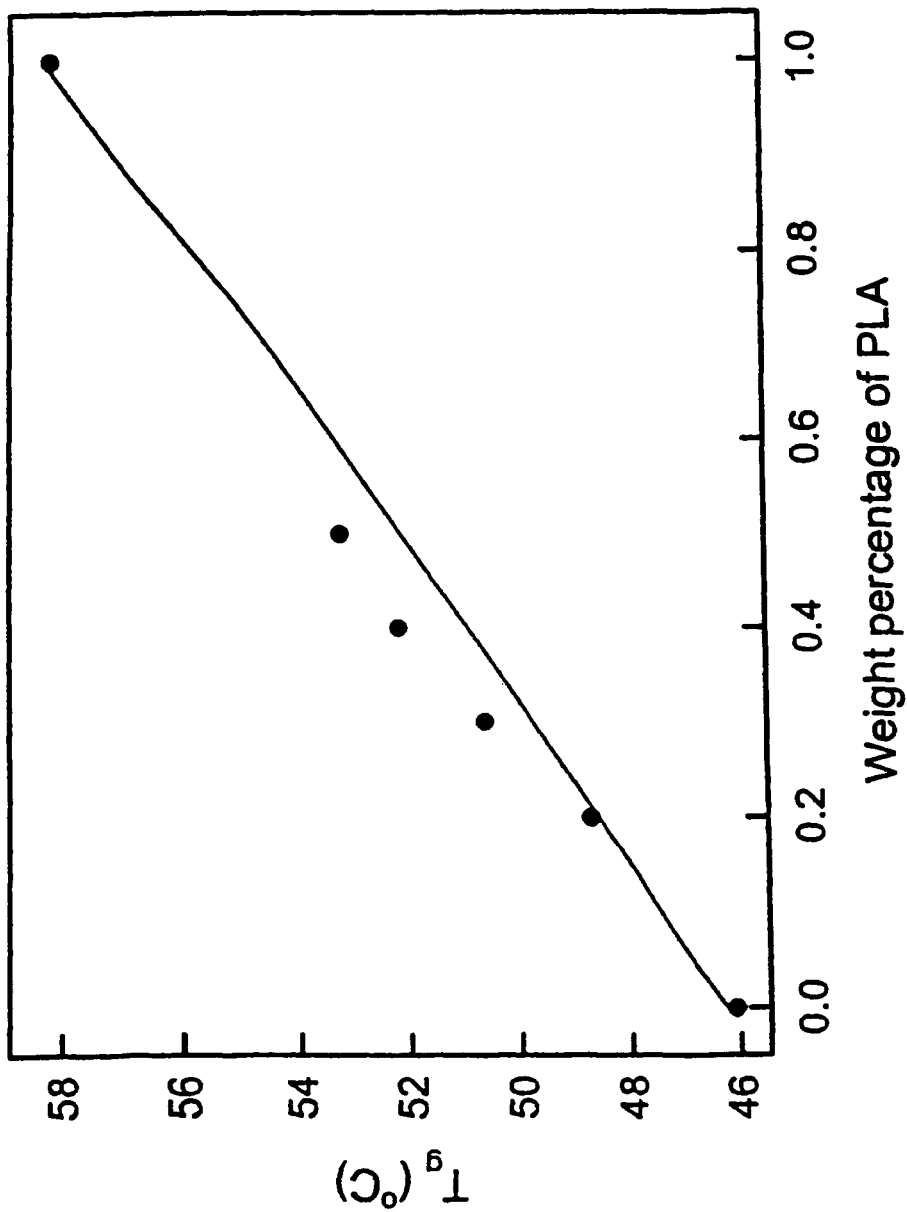
FIG. 38 shows glass transition temperatures measured following quenching of the PLA/PVAc blends (solid points). Solid line is best fit to the Fox equation, $1/T_g = w_a/T_g^a + w_b/T_g^b$.

The crystallization behavior selected of polymer blends was also analyzed. All of the samples were heat pressed at 180° C. for 10 minutes and then annealed at 110° C. for 1 hour before thermal analysis, providing a standard condition for extensive crystallization. FIG. 37 summarizes the first DSC heating trace of the samples measured after annealing. The results indicate that PVAc itself is amorphous (though with large physical aging content) but that incorporation of PLA leads to crystallization in proportion to the PLA wt-%. Also, the peak endotherm positions (melting transitions) shift slightly to higher temperatures with increasing PLA content. Quenching these samples to T=20° C. and reheating to 200° C. again showed clearly that single $T_g$'s are observed and that crystallization can be largely suppressed. Importantly for shape memory, the single glass transition events were not broadened in the blends relative to the pure components, suggesting that the amorphous phase was quite homogeneous for all of the blends. The observed $T_g$ values are plotted in FIG. 38 along with the best fit with the Fox equation, showing slight positive deviation. This leads to a conclusion that strong interactions between the two polymers that reduces free volume of the polymer blends and hence, increased glass transition temperature relative to the Fox equation prediction has occurred.

In order to elucidate the effect of PVAc on the degree of crystallinity and the crystal structures, the crystalline diffraction patterns were observed via wide-angle x-ray diffraction. The results indicate that the PVAc phase has only an amorphous halo, thus being totally amorphous, while the PLA exhibits three very strong diffraction peaks at 2θ=22.3°, 25.0° and 28.6°, corresponding to d-spacings of 5.92, 5.29, and 4.64 A°, respectively. Upon addition of PVAc, all of the peak intensities were depressed, but the peak positions remained essentially unchanged. Consistent with the DSC results, the degree of crystallinity increases in proportion to PLA addition. From the peak width at half height, it was found that the crystalline lamellae size did not decrease, although the degree of crystallinity decreased, with increasing PVAc content. This means that the decrease in crystallinity and depression of the melting transitions are not due to a change of crystal size, but rather may be due to a thinning of the lamellae thickness or to a decrease of the crystal concentration.

Figure 39:
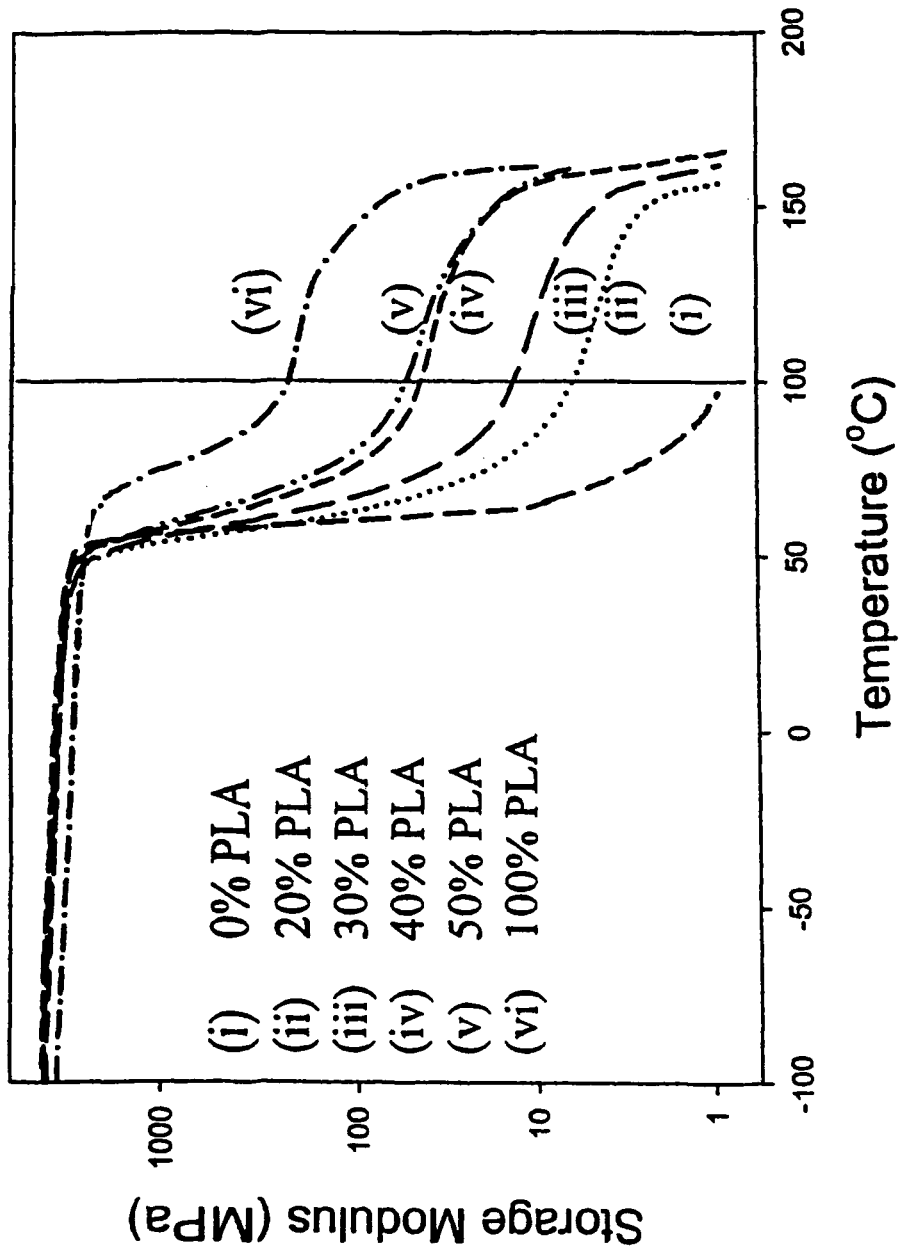
FIG. 39 shows tensile storage modulus versus temperature for a range of PLA/PVAc blends whose composition is indicated in the plot.

The storage modulus of the polymer blends was also measured using DMTA, first investigating the effects of annealing on the storage modulus. Below their glass transition temperatures, $T_g$, both samples exhibit similar high storage moduli (3 GPa), as well as similar softening points. When heated above $T_g$, the storage modulus of thermally quenched samples decreases sharply to about 2 MPa; however, further increasing the temperature induces a modulus increase attributed to recrystallization of the samples at higher temperatures. This also proved that the sample is not in an equilibrium state and that its mechanical properties in the rubbery region depend on thermal history. To reach equilibrium, the sample was annealed at 110° C. for 1 hour as previously described for DSC analyses. The storage modulus above $T_g$ shifts to about 200 MPa until melting, the increase being due to an increase of the degree of crystallinity on annealing to tune the rubbery modulus at equilibrium state. PLA was blended in different proportions to PVAc and annealed as above. Storage moduli for such blends were measured and the results are plotted in FIG. 39. It can be seen that, below $T_g$, all of the samples show similar large moduli while above $T_g$ the moduli decrease to a plateau whose magnitude depends on crystallinity and thus PLA content. This trend is in accordance with that of DSC and XRD, and can be explained by the fact that the increase of storage moduli came from the physical crosslinking formed by crystals and the filler effect of the high modulus crystalline phase.

Stress-free shape memory tests were carried out in hot water at 65° C., with an annealed sample composed of 30% PLA. The results show that the sample features quick and complete shape memory behavior: the sample recovers to the original shape (straight bar) within 10 seconds, with most of the recovery being accomplished within the first several seconds.

The same characterizations were carried out on the blends of PVDF and PVAc as above disclosed. The TGA and DSC results show that PVDF is also thermally stable up to 300° C., and the mixtures form only one glass transition, the values fall between the Tgs of the two homopolymers and changes with changing composition. At the same time, the melting points and the degrees of crystallinity were depressed with the incorporation of amorphous PVAc.

The storage moduli of the blends, which give the rigidity of the materials, were also measured. The results are similar to those of the PLA/PVAc blends, the PVDF/PVAc blends being very rigid below the critical temperatures ($T_g$), and featuring a sharp modulus changes at the Tg to a plateau modulus ranging from several MPa to tens of MPa, depending on the degree of crystallinity of the blends. These plateau moduli can be tuned by adjusting the degree of crystallinity of the blend, that is, adjust the blend composition.

The polymer in any of the above stents may be bioabsorbable or non-bioabsorbable. Bioabsorbable polymers include, for example, polyurethanes and polyurethane copolymers such as those described above with the general formula (directly below), where X/Y is, for example, 1 to 20, n is, for example, 2 to 1000, and the total degree of polymerization m is, for example, 2 to 100

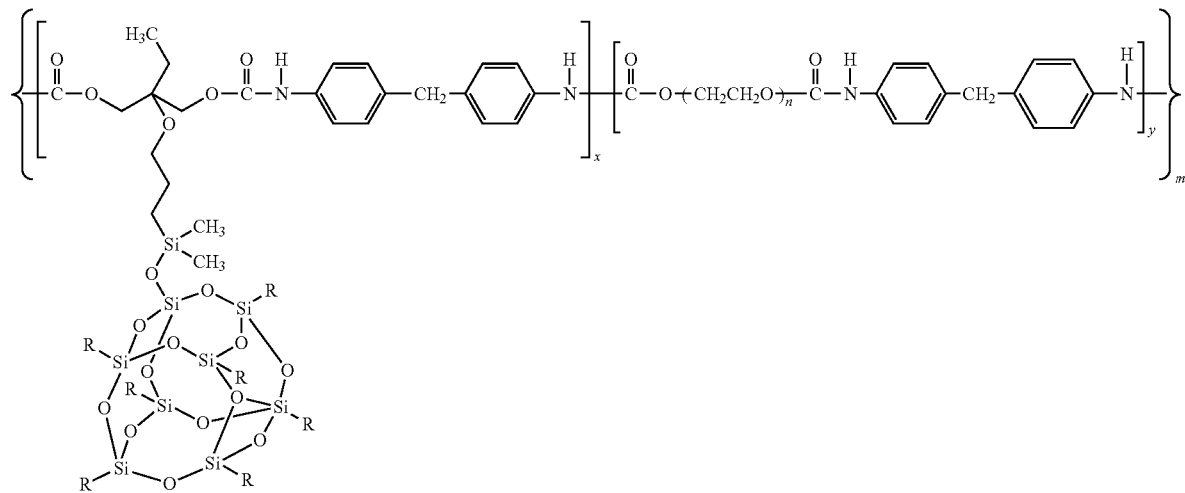

The bioabsorbability of the polymers is enhanced by copolymerization of polyurethane and POSS with suitable monomers. Examples of suitable monomers include caprolactone, ethyleneglycol, ethylene oxide, lactic acid, and glycolic acid. The copolymers from these monomers can hydrolyze and cleave the polymer linkage.

Other embodiments of stents can also be formed to include materials described above. In some embodiments, an implantable medical stent may be delivered into the body using a catheter. The stent can be delivered in a small diameter form and then expanded at a treatment site by triggering a shape change (for example, by heat application) caused by the shape memory properties of the polymer. The stent can also be expanded by a mechanical expander such as an inflatable balloon of the type used on an angioplasty catheter.

In some embodiments, the stent is sized (e.g., an expanded inner diameter of about 2 mm to about 20 mm) and configured for use in the vascular system, particularly the coronary arteries, and implanted after or simultaneously with an angioplasty procedure to maintain an open lumen and reduce restenosis. Vascular stents are described in U.S. Provisional Application No. 60/418,023, which is hereby incorporated in full by reference. For example, a stent for coronary use can have an initial diameter of about 2 mm, an expanded diameter of about 4 mm, and a wall thickness of about 0.005 mm to 0.1 mm. Other exemplary applications include neuro, carotid, peripheral, and vasculature lumens. The vascular stent can be bioabsorbable or non-bioabsorbable.

In other embodiments, a stent, e.g., a bioabsorbable or a non-bioabsorbable stent, is constructed for use in nonvascular lumens, such as the esophagus, ureteral, biliary, or prostate.

In other embodiments, the stent is conductive to allow an electrical current to pass through the stent, for example, to deliver electricity to an area of the body or to trigger, for example, a physical change in the stent, for example, a change in the diameter of the stent.

In still other embodiments, the stent, for example, of FIGS. 4, 23 and 26, is made porous by, for example, adding a chemical foaming agent to the polymer from which the stent is made during the production the plastic strand. In some implementations, the stent is porous and includes a medicament. The initial porosity of the stent can be reduced, for example, by the application of heat and pressure before deployment in the body. Upon deployment of the stent in the body, the porosity is increased by a triggering event, for example, the application of heat to the stent at the desired site of treatment.

What is claimed is:

1. A product comprising:
an endoprosthesis having a body formed of a non-bioabsorbable polymer comprising a cross-linked polycyclooctene, the polycyclooctene having been cross-linked while the endoprosthesis is in an expanded position to provide shape memory to the endoprosthesis, the endoprosthesis being designed for delivery into a body lumen and being in a collapsed state so that the endoprosthesis can be delivered into the body lumen, and wherein the endoprosthesis is capable of reverting from the collapsed state to the expanded state when warmed after delivery to a body lumen.

2. The product of claim 1, wherein the body has a wall having a wall thickness and wherein the wall thickness is maintained if the endoprosthesis reverts from the collapsed state to the expanded state.

3. The product of claim 2, wherein the change in the wall thickness is less than about 1%.

4. The product of claim 2, wherein the wall thickness is from about 0.005 mm to about 5 mm.

5. The product of claim 1, wherein the endoprosthesis is a stent.

6. The product of claim 1, wherein the endoprosthesis is capable of reverting from the collapsed state to the expanded state at a temperature below 60° C.

7. The product of claim 1, wherein the endoprosthesis is capable of reverting from the collapsed state to the expanded state at a temperature above 37° C.

8. The product of claim 1, wherein only a portion of the endoprosthesis is in a collapsed state that is capable of reverting to an expanded state when warmed.

9. The product of claim 1, wherein the polycyclooctene has been chemically cross-linked.

10. The product of claim 1, wherein the endoprosthesis has a tubular shape.

11. The product of claim 1, wherein the polycyclooctene has been radiation cross-linked.

12. The product of claim 1, wherein the polycyclooctene exhibits a plateau in its plot of storage modulus as a function of temperature.

13. The product of claim 1, wherein the endoprosthesis further includes radiopaque agent.

14. The product of claim 1, wherein the endoprosthesis further includes a drug.

15. The product of claim 1, wherein the body of the endoprosthesis is metal-free.

16. The product of claim 1, wherein the body of the endoprosthesis consists of the cross-linked polycyclooctene.

17. A product comprising:
a stent having a metal-free body formed of a non-bioabsorbable polymer comprising a cross-linked polycyclooctene, the polycyclooctene having been cross-linked while the stent is in an expanded position to provide shape memory to the stent, the stent being designed for delivery into a body lumen and being in a collapsed state so that the stent can be delivered into the body lumen, and wherein the stent is capable of reverting from the collapsed state to the expanded state when warmed after delivery to a body lumen.

18. The product of claim 17, wherein the wall thickness is from about 0.005 mm to about 5 mm.

19. A product comprising:
a stent having a body consisting of non-bioabsorbable cross-linked polycyclooctene, the polycyclooctene having been cross-linked while the stent is in an expanded position to provide shape memory to the stent, the stent being designed for delivery into a body lumen and being in a collapsed state so that the stent can be delivered into the body lumen, and wherein the stent is capable of reverting from the collapsed state to the expanded state when warmed after delivery to a body lumen.

20. The product of claim 19, wherein the wall thickness is from about 0.005 mm to about 5 mm.

* * * * *